US009351492B2

(12) United States Patent
Quave et al.

(10) Patent No.: US 9,351,492 B2
(45) Date of Patent: May 31, 2016

(54) ANTI-BIOFILM COMPOSITIONS AND METHODS FOR USING

(71) Applicant: Board of Trustees University of Arkansas, Little Rock, AR (US)

(72) Inventors: Cassandra L. Quave, Little Rock, AR (US); Mark S. Smeltzer, Little Rock, AR (US); Cesar M. Compadre, Little Rock, AR (US); Howard Hendrickson, Little Rock, AR (US)

(73) Assignee: BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 56 days.

(21) Appl. No.: 14/243,406

(22) Filed: Apr. 2, 2014

(65) Prior Publication Data

US 2014/0271777 A1 Sep. 18, 2014

Related U.S. Application Data

(62) Division of application No. 13/267,696, filed on Oct. 6, 2011, now Pat. No. 8,741,855.

(60) Provisional application No. 61/488,878, filed on May 23, 2011, provisional application No. 61/390,254, filed on Oct. 6, 2010.

(51) Int. Cl.
| | | |
|---|---|---|
| *A01N 43/90* | (2006.01) | |
| *A61K 31/335* | (2006.01) | |
| *A61K 31/35* | (2006.01) | |
| *A01N 65/00* | (2009.01) | |
| *A01N 65/34* | (2009.01) | |
| *A61K 31/19* | (2006.01) | |
| *A61K 31/192* | (2006.01) | |
| *A61K 31/352* | (2006.01) | |
| *A61K 31/366* | (2006.01) | |
| *A61K 31/43* | (2006.01) | |
| *A61K 31/431* | (2006.01) | |
| *A61K 31/496* | (2006.01) | |
| *A61K 31/65* | (2006.01) | |
| *A61K 31/7048* | (2006.01) | |
| *A61K 31/7056* | (2006.01) | |
| *A61K 36/75* | (2006.01) | |
| *A61K 36/76* | (2006.01) | |
| *A61K 36/77* | (2006.01) | |
| *A61K 36/87* | (2006.01) | |
| *A61K 36/88* | (2006.01) | |
| *A61K 36/896* | (2006.01) | |
| *A61K 38/12* | (2006.01) | |
| *A61K 38/14* | (2006.01) | |
| *A61K 38/15* | (2006.01) | |
| *A61K 36/185* | (2006.01) | |
| *A61K 36/21* | (2006.01) | |
| *A61K 36/23* | (2006.01) | |
| *A61K 36/24* | (2006.01) |
| *A61K 36/28* | (2006.01) |
| *A61K 36/40* | (2006.01) |
| *A61K 36/45* | (2006.01) |
| *A61K 36/48* | (2006.01) |
| *A61K 36/49* | (2006.01) |
| *A61K 36/51* | (2006.01) |

(Continued)

(52) U.S. Cl.
CPC ............... *A01N 43/90* (2013.01); *A01N 65/00* (2013.01); *A01N 65/34* (2013.01); *A61K 31/19* (2013.01); *A61K 31/192* (2013.01); *A61K 31/352* (2013.01); *A61K 31/366* (2013.01); *A61K 31/43* (2013.01); *A61K 31/431* (2013.01); *A61K 31/496* (2013.01); *A61K 31/65* (2013.01); *A61K 31/7048* (2013.01); *A61K 31/7056* (2013.01); *A61K 36/185* (2013.01); *A61K 36/21* (2013.01); *A61K 36/23* (2013.01); *A61K 36/24* (2013.01); *A61K 36/28* (2013.01); *A61K 36/40* (2013.01); *A61K 36/45* (2013.01); *A61K 36/48* (2013.01); *A61K 36/49* (2013.01); *A61K 36/51* (2013.01); *A61K 36/52* (2013.01); *A61K 36/53* (2013.01); *A61K 36/57* (2013.01); *A61K 36/61* (2013.01); *A61K 36/73* (2013.01); *A61K 36/75* (2013.01); *A61K 36/76* (2013.01); *A61K 36/77* (2013.01); *A61K 36/87* (2013.01); *A61K 36/88* (2013.01); *A61K 36/896* (2013.01); *A61K 38/12* (2013.01); *A61K 38/14* (2013.01); *A61K 38/15* (2013.01)

(58) Field of Classification Search
None
See application file for complete search history.

(56) References Cited

U.S. PATENT DOCUMENTS 6,352,727 B1 3/2002 Takahashi
7,604,978 B2 10/2009 Eldridge
(Continued)

FOREIGN PATENT DOCUMENTS

WO 2009/114810 A2 9/2009
WO 2012/048119 A1 4/2012

OTHER PUBLICATIONS

A. Lemke et al., "Amphotericin B," Appl Microbiol Biotechnol (2005) 68: 151-162.*
(Continued)

*Primary Examiner* — Tracy Vivlemore
*Assistant Examiner* — Monica Shin
(74) *Attorney, Agent, or Firm* — Polsinelli PC

(57) ABSTRACT

The present invention provides polyphenolic compositions derived from a plant that inhibit the formation of a biofilm. Also provided are combinations that comprise at least one phenolic phytochemical and at least one antimicrobial agent that inhibit the growth of an established biofilm. Further, the present invention provides methods for inhibiting the formation and growth of biofilms.

8 Claims, 21 Drawing Sheets

(51) Int. Cl.
  A61K 36/52  (2006.01)
  A61K 36/53  (2006.01)
  A61K 36/57  (2006.01)
  A61K 36/61  (2006.01)
  A61K 36/73  (2006.01)

(56) References Cited

U.S. PATENT DOCUMENTS

| | | | |
|---|---|---|---|
| 7,612,045 | B2 | 11/2009 | Eldridge |
| 7,691,418 | B2 | 4/2010 | Rossel |
| 2002/0051825 | A1 | 5/2002 | Unno et al. |
| 2004/0156925 | A1 | 8/2004 | Howell et al. |
| 2006/0018842 | A1 | 1/2006 | Blumenthal |
| 2008/0280994 | A1 | 11/2008 | Zhang et al. |
| 2009/0004302 | A1 | 1/2009 | Cyr |
| 2010/0173860 | A1 | 7/2010 | Seeram et al. |
| 2010/0189824 | A1 | 7/2010 | Arntzen et al. |
| 2010/0285084 | A1* | 11/2010 | Yang et al. ............ 424/423 |
| 2011/0105421 | A1* | 5/2011 | Mathee et al. .......... 514/29 |
| 2012/0088671 | A1 | 4/2012 | Quave et al. |

OTHER PUBLICATIONS

M. M Webb, "Way of the future? Daptomycin use in bacteraemia and infective endocarditis. A review of the literature." The New Zealand Medical Student Journal No. 17, Jul. 2013, pp. 13-15.*
S. Cole et al., "Characterization of Monospecies Biofilm Formation by Helicobacter pylori," Journal of Bacteriology, vol. 186, No. 10, May 2004, p. 3124-3132.*
"Antimicrobial", Collins English Dictionary—Complete and Unabridged, <http://www.thefreedictionary.com/antimicrobial+agent>, HarperCollins Publishers, 2003, 3 pgs.
Badria et al., "Natural Products for Dental Caries Prevention", Journal of Medicinal Food, 2004, pp. 381-384, vol. 7, No. 3.
Beenken et al., "Mutation of sarA in Staphylococcus aureus Limits Biofilm Formation", Infection and Immunity, 2003, pp. 4206-4211, vol. 71, No. 7.
Beenken et al., "Epistatic Relationships between sarA and agr in Staphylococcus aureus Biofilm Formation", PLoS ONE, 2010, 13 pgs., vol. 5, No. 5: e10790.
"Biofilms—The New Microbial Order", Center for Medical Mycology, <http://medicalmycology.org/biofilms.htm>, Jun. 26, 2012, 6 pgs.
Chandra et al., "Biofilm Formation by the Fungal Pathogen Candida albicans: Development, Architecture, and Drug Resistance", Journal of Bacteriology, 2001, pp. 5385-5394, vol. 183, No. 18.
Dall'Acqua et al., "Evaluation of in vitro antioxidant properties of some traditional Sardinian medicinal plants: Investigation of the high antioxidant capacity of Rubus ulmifolius", Food Chemistry, 2008, pp. 745-749, vol. 106.
Dixon et al., "Chapter 76: Antifungal Agents", Medical Microbiology, 4th edition, Galveston (TX): University of Texas Medical Branch at Galveston, 1996, 5 pgs.
Durig et al., "Chemoinformatics-assisted development of new antibiofilm compounds", Applied Microbiology and Biotechnology, 2010, pp. 309-317, vol. 87.
Elkhateeb et al., "Anti-babesial ellagic acid rhamnosides from the bark of Elaeocarpus parvifolius", Phytochemistry, 2005, pp. 2577-2580, vol. 66, No. 21.
European Office Action from related European Patent Application No. 11831602.5, dated Apr. 8, 2014, 14 pgs.
Flamini et al., "Three anthrones from Rubus ulmifolius", Phytochemistry, 2002, pp. 873-876, vol. 59.
Fogliani et al., "Bioactive ellagitannins from Cunonia macrophylla, an endemic Cunoniaceae from New Caledonia", Phytochemistry, 2005, pp. 241-247, vol. 66, No. 2.
Gibbons et al., "The genus Hypericum—a valuable resource of anti-Staphylococcal leads", Fitoterapia, 2002, pp. 300-304, vol. 73.
Gibbons, "Anti-Staphylococcal plant natural products", Natural Products Reports, 2004, pp. 263-277, vol. 21.
Gibbons, "Phytochemicals for Bacterial Resistance—Strengths, Weaknesses and Opportunities", Planta Medica, 2008, pp. 594-602, vol. 74.
Hancock et al., "Dietary plant components ellagic acid and tannic acid inhibit Escherichia coli biofilm formation", Journal of Medical Microbiology, 2010, pp. 496-498, vol. 59.
Huber et al., "Influence of Polyphenols on Bacterial Biofilm Formation and Quorum-sensing", Inhibition of Polyphenols, Zeitschrift fur Naturforschung, Journal of Biosciences, 2003, pp. 879-884, vol. 58c.
Imai et al., "Extractives of Quercus crispula sapwood infected by the pathogenic fungi Raffaelea quercivora I: comparison of sapwood extractives from noninfected and infected samples", Journal of Wood Science, 2009, pp. 126-132, vol. 55, No. 2.
International Search Report and Written Opinion from related PCT Application No. PCT/US2011/055119, mailed May 18, 2012, 11 pgs.
Jang et al., "An Ellagic Acid Rhamnoside from the Roots of Potentilla discolor with Protein Glycation and Rat Lens Aldose Reductase Inhibitory Activity", Natural Product Sciences, 2007, pp. 160-163, vol. 13, No. 2.
Kim et al., "Ellagic acid rhamnosides from the stem bark of Eucalyptus globulus", Phytochemistry, 2001, pp. 587-591, vol. 57, No. 4.
King et al., "Characteristics and occurrence of phenolic phytochemicals", Journal of the American Dietetic Association, 1999, pp. 213-218, vol. 99, No. 2.
Kuete et al., "Antimycobacterial, antibacterial and antifungal activities of Terminalia superba (Combretaceae)", South African Journal of Botany, 2010, pp. 125-131, vol. 76, No. 1.
Landete, "Ellagitannins, ellagic acid and their derived metabolites: A review about source, metabolism, functions and health", Food Research International, 2011, pp. 1150-1160, vol. 44.
Losso et al., "In vitro anti-proliferative activities of ellagic acid", Journal of Nutritional Biochemistry, 2004, pp. 672-678, vol. 15.
Lu et al., "Ellagic Acid Inhibits Growth and Arylamine N-Acetyltransferase Activity and Gene Expression in Staphylococcus aureus", in vivo, 2005, pp. 195-200, vol. 19.
Marsh, "Dental Plaque as a Biofilm: The Significance of pH in Health and Caries", Compendium, 2009, pp. 76-87, vol. 30, No. 2.
Martini et al., "Antimicrobial activity against Helicobacter pylori strains and antioxidant properties of blackberry leaves (Rubus ulmifolius) and isolated compounds", International Journal of Antimicrobial Agents, 2009, pp. 50-59, vol. 34, No. 1.
Matthew et al., "Ellagic acid glycosides from Turpinia ternata", Natural Product Research, 2007, pp. 83-88, vol. 21, No. 1.
"Microorganism", Collins English Dictionary—Complete and Unabridged, <http://www.thefreedictionary.com/microorganisms>, HarperCollins Publishers, 2003, 4 pgs.
Ndukwe et al., "Pharmacological activity of 2,3,8-tri-O-methyl ellagic acid isolated from the stem bark of Irvingia gabonensis", African Journal of Biotechnology, 2007, pp. 1910-1912, vol. 6, No. 16.
Ohemeng et al., "DNA gyrase inhibitory and antibacterial activity of some flavones(1)", Bioorganic & Medicinal Chemistry Letters, 1993, pp. 225-230, vol. 3, No. 2.
Panizzi et al., "In vitro antimicrobial activity of extracts and isolated constituents of Rubus ulmifolius", Journal of Ethnopharmacology, 2002, pp. 165-168, vol. 79.
Prosser et al., "Method of Evaluating Effects of Antibiotics on Bacterial Biofilm", Antimicrobial Agents and Chemotherapy, 1987, pp. 1502-1506, vol. 31, No. 10.
Quave et al., "Effects of extracts from Italian medicinal plants on planktonic growth, biofilm formation and adherence of methicillin-resistant Staphylococcus aureus", Journal of Ethnopharmacology, 2008, pp. 418-428, vol. 118.
Quave et al., "Ellagic Acid Derivatives from Rubus ulmifolius Inhibit Staphylococcus aureus Biofilm Formation and Improve Response to Antibiotics", PLoS ONE, 2012, e28737, pp. 1-16, vol. 7, No. 1.
Rabea et al., "Chitosan as Antimicrobial Agent: Applications and Mode of Action", Biomacromolecules, American Chemical Society, 2003, pp. 1457-1465, vol. 4, No. 6.
Rahman et al., "New Antioxidant and Antimicrobial Ellagic Acid Derivatives from Pteleopsis hylodendron", Planta Medica, 2001, pp. 335-339, vol. 67, No. 4.

(56) References Cited

OTHER PUBLICATIONS

Ren et al., "Inhibition of biofilm formation and swarming of Bacillus subtilis by (5Z)-4-bromo-5-(bromomethylene)-3-butyl-2(5H)-furanone", Letters in Applied Microbiology, 2002, pp. 293-299, vol. 34.

Sgariglia et al., "Isolation of antibacterial components from infusion of Caesalpinia paraguariensis bark. A bio-guided phytochemical study", Food Chemistry, 2010, pp. 395-404, vol. 126, No. 2.

Simoes-Pires et al., "Ellagic Acid Derivatives from Syzygium cumini Stem Bark: Investigation of their Antiplasmodial Activity", Natural Product Communications, 2009, pp. 1371-1376, vol. 4, No. 10.

Supplementary European Search Report and Written Opinion from related European Application No. EP 11831602.5, dated Aug. 2, 2013, 19 pgs.

Thiem et al., "Antimicrobial activity of Rubus chamaemorus leaves", Fitoterapia, 2004, pp. 93-95, vol. 75, No. 1.

Weiss et al., "Impact of sarA on Antibiotic Susceptibility of Staphylococcus aureus in a Catheter-Associated In Vitro Model of Biofilm Formation", Antimicrobial Agents and Chemotherapy, 2009, pp. 2475-2482, vol. 53, No. 6.

Weiss et al., "Impact of sarA on Daptomycin Susceptibility of Staphylococcus aureus Biofilms In Vivo", Antimicrobial Agents and Chemotherapy, 2009, pp. 4096-4102, vol. 53, No. 10.

Zhou et al., "Two ellagic acid glycosides from Gleditsia sinensis Lam. with antifungal activity on Magnaporthe grisea", Natural Product Research, 2007, pp. 303-309, vol. 21, No. 4.

Non-Final Office Action from related U.S. Appl. No. 13/267,696, dated Dec. 12, 2012, 10 pgs.

Non-Final Office Action from related U.S. Appl. No. 13/267,696, dated Jun. 18, 2013, 20 pgs.

Notice of Allowance and Fee(s) Due from related U.S. Appl. No. 13/267,696, dated Jan. 22, 2014, 6 pgs.

\* cited by examiner

US 9,351,492 B2

ANTI-BIOFILM COMPOSITIONS AND METHODS FOR USING

CROSS REFERENCE TO RELATED APPLICATIONS

This application is a divisional of U.S. patent application Ser. No. 13/267,696, filed Oct. 6, 2011, which claims the priority of U.S. Provisional Application No. 61/488,878, filed May 23, 2011, and U.S. Provisional Application No. 61/390,254, filed Oct. 6, 2010, each of which is hereby incorporated by reference in its entirety.

FIELD OF THE INVENTION

The present invention generally relates to biofilms. In particular, it relates to compositions and methods for inhibiting biofilm formation and/or reducing the growth of an established biofilm.

BACKGROUND OF THE INVENTION

*Staphylococcus aureus* is arguably the most problematic pathogen faced by modern healthcare systems today, owing in large part to the persistent emergence of antibiotic resistant strains. This is perhaps most evident in the recent appearance of methicillin-resistant strains even among isolates causing community-acquired infection. Moreover, many of these strains, most notably those of the USA300 clonal lineage, have the capacity to cause serious, life-threatening infection even in otherwise healthy individuals. This accounts in large part for the observation that, in the United States alone in 2005, an estimated 94,360 patients suffered from invasive infection caused by methicillin-resistant *S. aureus* (MRSA), with approximately 18,650 resulting in a fatal outcome.

The continued emergence of antibiotic-resistant strains has created an urgent need for new antimicrobial agents. However, many *S. aureus* infections are recalcitrant to antimicrobials even in the absence of issues related to acquired resistance. A primary contributing factor to this recalcitrance is formation of a biofilm on both native tissues and indwelling medical devices. This is due to the fact that the biofilm confers a degree of intrinsic resistance that often necessitates surgical intervention to debride infected tissues and/or remove infected devices. For example, one study found that nearly half of patients with implanted orthopedic devices admitted to a hospital with *S. aureus* bacteremia had developed an implant-associated infection. Thus, while there is an urgent need for new antibiotics, there is an equally urgent need to develop therapeutic agents that could be used to limit biofilm formation. While such agents would not necessarily function as antibiotics in and of themselves, they could be used as a prophylactic to limit biofilm formation (e.g. coating for implanted devices, surgical lavage, or pre-operative oral prophylaxis) or as a therapeutic to be used in conjunction with more conventional antibiotics to treat an established biofilm-associated infection.

SUMMARY OF THE INVENTION

Among the various aspects of the present disclosure is the provision of a polyphenolic composition. The polyphenolic composition is prepared by a process comprising (a) partitioning an alcohol extract of a plant with a mixture of water and hexane to form a first water partition and a hexane partition; (b) partitioning the first water partition with a mixture of water and ethyl acetate to form a second water partition and a ethyl acetate partition; (c) partitioning the second water partition with a mixture of water and butanol to form a third water partition and a butanol partition; and (d) fractionating the butanol partition by column chromatography with a mobile phase comprising a mixture of methanol and dichloromethane, wherein the polyphenolic composition is eluted by the mobile phase in which the volume ratio of methanol to dichloromethane is about 40:60.

Another aspect of the disclosure provides a combination comprising at least one phenolic phytochemical and at least one antimicrobial agent.

Still another aspect of the disclosure encompasses a method for inhibiting formation of a biofilm. The method comprises contacting a plurality of free floating microorganisms with the polyphenolic composition detailed above or a fraction thereof such that formation of the biofilm is inhibited.

A further aspect of the disclosure provides a method for inhibiting growth of an established biofilm. The method comprises contacting the biofilm with at least one phenolic phytochemical and at least one antimicrobial agent such that the biofilm has a reduced number of microorganisms.

Other features and iterations of the invention are described in more detail below.

DETAILED DESCRIPTION OF THE INVENTION

Figure 1:
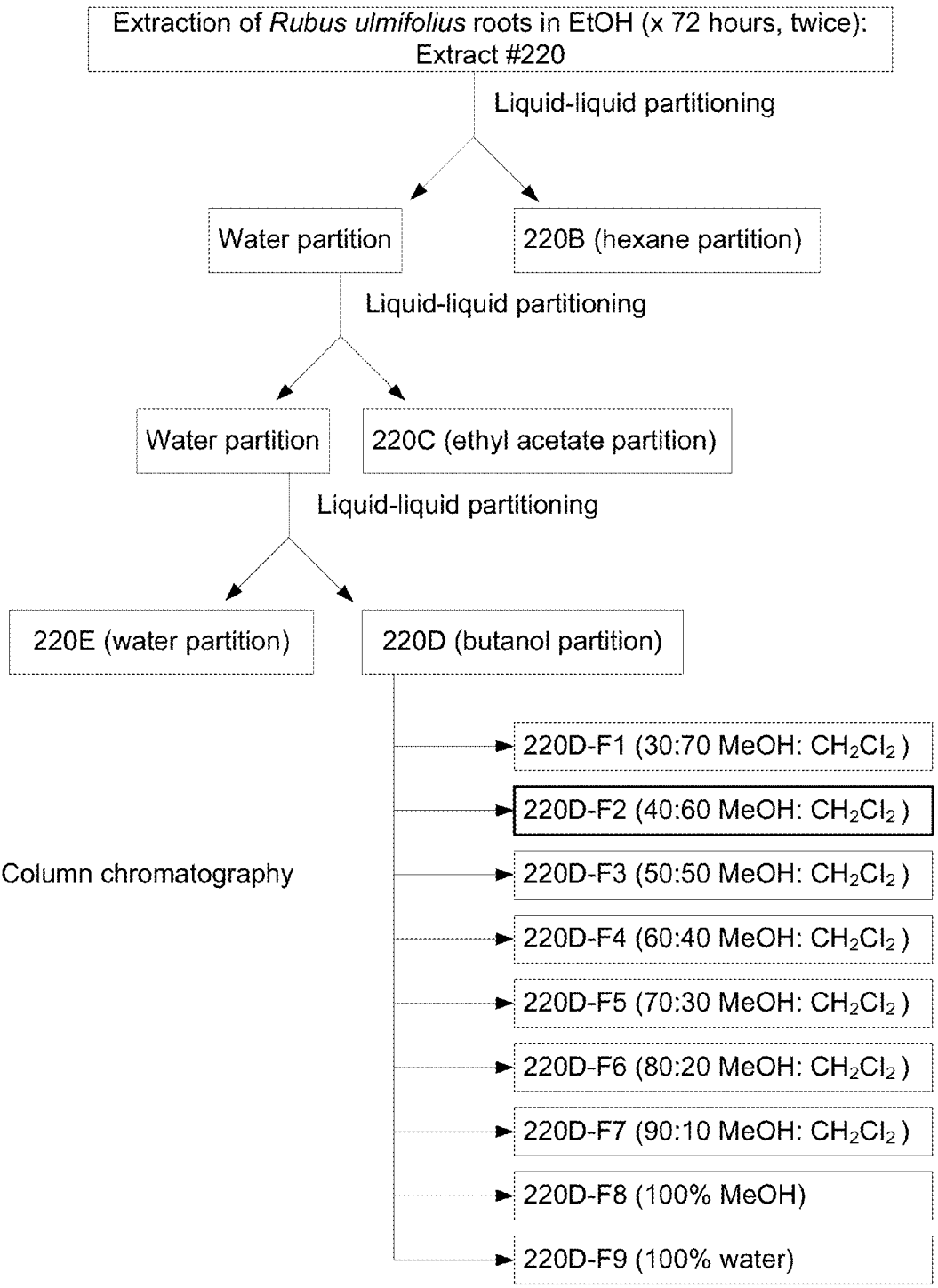
FIG. 1 presents the fractionation scheme for extraction of the phenolic-rich fraction of *R. ulmifolius*.

The present invention provides compositions and methods for inhibiting the formation and growth of biofilms. In one aspect, the disclosure provides a polyphenolic composition comprising ellagic acid and ellagic acid derivatives. The phenolic composition is derived from a plant extract by a process disclosed herein. It has been discovered that the polyphenolic composition inhibits biofilm formation and increases susceptibility of an established biofilm to antimicrobial agents. Another aspect of the disclosure provides a combination comprising at least one phenolic phytochemical and at least one antimicrobial agent, wherein the combination inhibits the growth of established biofilms. Advantageously, the activity of the combination disclosed herein is synergistic, i.e., its activity is more than the sum of the activity of each individual component. Also provided herein are methods for inhibiting the formation of a biofilm, as well as methods inhibiting the growth of an established biofilm.

(I) Polyphenolic Composition

In one embodiment a polyphenolic composition is provided. The polyphenolic composition is prepared by a process comprising (a) partitioning an alcohol extract of a plant with a mixture of water and hexane to form a first water partition and a hexane partition; (b) partitioning the first water partition with a mixture of water and ethyl acetate to form a second water partition and a ethyl acetate partition; (c) partitioning the second water partition with a mixture of water and butanol to form a third water partition and a butanol partition; and (d) fractionating the butanol partition by column chromatography with a mobile phase comprising a mixture of methanol and dichloromethane, wherein the polyphenolic composition is eluted by the mobile phase in which the volume ratio of methanol to dichloromethane is about 40:60.

The method comprises a series of steps such that a fraction enriched with a polyphenolic composition may be isolated from an alcohol extract of a plant.

(a) Alcohol Extract

The alcohol extract may be derived from a plant belonging to a variety of plant families. Non-limiting examples of suitable plant families include Rosaceae, Fagaceae, Salicaceae, Myrtaceae, Vitaceae, Ericaceae, Combretaceae, Elaeocarpaceae, Lythraceae, Symplocaceae, Hypoxidaceae, Amaranthaceae, Juncaceae, Juglandaceae, Sapindaceae, Lamiaceae, Magnoliaceae, Gentianaceae, Apocynaceae, Moringaceae, Apiaceae, Rutaceae, Aquafoliaceae, Santalaceae, Cornaceae, Asteraceae, Bignoniaceae, and Fabaceae. Preferred plant families include Rosaceae, Fagaceae, Salicaceae, Myrtaceae, Vitaceae, Ericaceae, Combretaceae, and Juglandaceae. In some embodiments, the plant may be *Castanea sativa, Quercus cerris, Juglans regia, Vitis vinefera, Crataegus monogyna, Prunus spinosa, Rosa canina*, or *Rubus ulmifolius*. In some embodiments, the plant family may be Rosaceae. In an exemplary embodiment, the plant may be *Rubus ulmifolius*.

A variety of plant parts may be used to arrive at the alcohol extract. Suitable plant parts include roots, bulbs, tubers, leaves, basal leaves, stems, stem nodes, stem internodes, galls, stalks, woody parts, flowers, inflorescences, fruits, infructescences, seeds, and combinations thereof. The plant part may be fresh, dried, frozen, or lyophilized. The plant part may be ground or pulverized into a plant material using a homogenizer, a blender, a mortar and pestle, a sonicator, or a similar apparatus.

The plant extract typically is prepared by contacting the plant material with an alcohol solvent for an appropriate period of time. Non-limiting examples of suitable alcohol solvents include methanol, ethanol, propanol, butanol, or combinations thereof. In preferred embodiments, the solvent may be ethanol such that the alcohol extract is an ethanol extract. The concentration of alcohol that is contacted with the plant material may range from about 1% to about 100%. In embodiments in which ethanol is the solvent, the concentration of ethanol may range from about 1% to about 20%, from about 20% to about 40%, from about 40% to about 60%, from about 60% to about 80%, or from about 80% to about 100%. In an exemplary embodiment, the concentration of ethanol may be about 95%.

The period of time the plant material is contacted with the alcohol solvent may range from about 1 hour to about 5 days. In various embodiments, the plant material may be contacted with the alcohol solvent for about 1-24 hours, for about 24-48 hrs, for about 48-72 hours, for about 72-96 hours, or for about 96-120 hours. In an exemplary embodiment, the period of time the plant material is contacted with the alcohol solvent may be about 72 hours. Upon removal of the extract from the plant material, the plant material may be extracted one or more additional times with fresh alcohol solvent, essentially as detailed above.

The alcohol solvent may be removed from the plant alcohol extract to form a dry plant alcohol extract. Those of skill in the art are familiar with suitable techniques to remove the alcohol solvent including, without limit, evaporation, distillation, and lyophillization.

(b) Liquid Extractions

The process for preparing a fraction rich in the polyphenolic compounds comprises subjecting the plant alcohol extract to a series of liquid extractions such that the polyphenolic compounds are partitioned into one of the phases and the other compounds are partitioned into the other phase. In general, the series of liquid extractions comprises contacting the plant alcohol extract (or partition thereof) with a solvent system, wherein the polarity of one or more of the solvents changes during each successive series of extractions. Those of skill in the art are familiar with liquid extraction protocols and suitable solvent systems. Generally, the liquids are mixed by gentle inversion at room temperature. After separation of the phases, the phase containing the polyphenolic compounds thereof may be extracted one or more times with the solvents of interest.

For example, the first step of the process may comprise a liquid extraction during which the plant alcohol extract is partitioned in a mixture of water and an alkane to form a first water partition and an alkane partition. Typically, the polyphenolic compounds are partitioned into the water phase upon extraction with a mixture of water and alkane. The alkane typically will comprise from five to ten carbons, and may be linear or branched. Suitable alkanes include, without limit, pentane, hexane, heptane, octane, and combinations thereof. An exemplary alkane is hexane.

In the next step of the process, for example, the first water partition may be extracted in a mixture of water and a non-polar solvent to form a second water partition and a non-polar solvent partition. Generally, the polyphenolic compounds are partitioned into the water phase upon extraction with a mixture of water and non-polar solvent. In various embodiments, the non-polar solvent may be ethyl acetate, butyl acetate, chloroform, diethyl ether, or combinations thereof. An exemplary non-polar solvent is ethyl acetate.

The next and final extraction step, for example, may comprise extracting the second water partition with a mixture of water and an alcohol to form a third water partition and an alcohol partition. Typically, the polyphenolic compounds are partitioned into the alcohol phase upon extraction with a mixture of water and alcohol. The alcohol may comprise from one to ten carbons, and may be linear or branched. Non-limiting examples of suitable alcohols include methanol, ethanol, propanol, isopropanol, butanol, pentanol, hexanol, and heptanol. An exemplary alcohol is butanol.

In a preferred embodiment, the first liquid-liquid extraction comprises water and hexane, the second liquid-liquid extraction comprises water and ethyl acetate, and the third liquid-liquid extraction comprises water and butanol.

(c) Column Chromatography

The method may further comprise fractionating the polyphenolic-rich fraction by column chromatography. Typically, the column will comprise an inorganic stationary phase. Non-limiting examples of suitable inorganic stationary phase materials include silica-based materials, silica gel, magnetic silica particles, glass powder, diatomaceous earth, zeolites, aluminium oxides, silicon oxides, titanium oxides, zirconium oxides, and hydroxyapatite. In an exemplary embodiment, the column chromatography comprises a silica gel stationary phase.

The mobile phase may comprise a mixture of methanol and dichloromethane. Those of skill in the art will appreciate that other mobile phases may be used to separate the polyphenolic composition from the other compounds. In embodiments in which the mobile phase comprises methanol and dichloromethane, the concentration of dichloromethane in the mobile phase typically decreases during the fractionation while the concentration of methanol in the mobile phase increases during the fractionation. The phenolic-rich fraction generally elutes from the column with a volume ratio of methanol to dichloromethane from about 30:70 to about 70:30. For example, the volume ratio of methanol to dichloromethane that elutes a phenolic-rich fraction may range from about 30:70, 32.5:67.5. 35:65, 37.5:62.5, 40:60, 42.5:57.5, 45:55, 47.5:52.5, 50:50, 52.5:47.5, 55:45, 57.5:42.5, 60:40, 62.5:37.5, 65:35, 67.5:32.5, or 70:30. In preferred embodiments, the polyphenolic-rich fraction may elute from the column at a volume ratio of methanol to dichloromethane of about 40:60, 50:50, or 60:40. In an exemplary embodiment, the polyphenolic-rich fraction may elute from the column at a volume ratio of methanol to dichloromethane of about 40:60. The polyphenolic-rich fraction may be dried by removing the mobile phase solvents using standard procedures.

(d) Compounds in the Polyphenolic Composition

The polyphenolic composition comprises ellagic acid and ellagic acid derivatives (see Example 6). The ellagic acid derivative may be methylated, acetylated, sulfated, phosphorylated, hydroxylated, glycosylated, or modified with another suitable group. Non-limiting examples of suitable glycosylated derivatives include methylated derivatives, acetylated derivatives, arabinopyranoside derivatives, galactoside derivatives, glucopyranoside derivatives, glucoside derivatives, glucuronide derivatives, glycoside derivatives, mannopyranoside derivatives, rhamnoside derivatives, xylofuranoside derivatives, and xylopyranoside derivatives. Exemplary ellagic acid derivatives include ellagic acid xylopyranoside, ellagic acid xylofuranoside, ellagic acid mannopyranoside, and ellagic acid rhamnoside. The polyphenolic composition may further comprise at least one sapogenin.

In some aspects, the polyphenolic composition may further comprise at least one compound chosen from [1]benzopyrano[5,4,3-cde][1]benzopyran-5,10-dione, 2-[(6-deoxy-α-L-mannopyranosyl)oxy]-3,7,8-trihydroxy-; [1]benzopyrano[5,4,3-cde][1]benzopyran-5,10-dione, 2,8-dihydroxy-3-methoxy-7-(D-xylopyranosyloxy)-; [1]benzopyrano[5,4,3-cde][1]benzopyran-5,10-dione, 2,3-dihydroxy-8-methoxy-7-(D-xylopyranosyloxy)-; [1]benzopyrano[5,4,3-cde][1]benzopyran-5,10-dione, 2-(α-L-arabinofuranosyloxy)-3,7-dihydroxy-8-methoxy-; 2-butenedioic acid, 2-[(2R,3R)-3,4-dihydro-5,7-dihydroxy-3-[(3,4,5-trihydroxybenzoyl)oxy]-2H-1-benzopyran-2-yl]-,(2Z)-; 5H,13H-bis[1,3]dioxolo[4,5]furo[3,2-h:2',3'-s][1,4,7,11,14,17]hexaoxacycloeicosin; 5H-benzocycloheptene-8,9-dicarboxylic acid, 2,3,4-tris(acetyloxy)-6-hydroxy-5-oxo-, 8-methyl ester; 1,4-Naphthalenedione, 2,3,5,6,8-pentakis(acetyloxy)-; L-ascorbic acid, 6,6'-(1,4-benzenedicarboxylate); D-glucose, cyclic 2,3-(4,4',5,5',6,6'-hexahydroxy[1,1'-biphenyl]-2,2'-dicarboxylate); D-glucose, cyclic 2,4-(4,4',5,5',6,6'-hexahydroxy[1,1'-biphenyl]-2,2'-dicarboxylate; D-glucose, cyclic 3,4-[4,4',5,5',6,6'-hexahydroxy[1,1'-biphenyl]-2,2'-dicarboxylate]; D-glucose, cyclic 3,6-(4,4',5,5',6,6'-hexahydroxy[1,1'-biphenyl]-2,2'-dicarboxylate); D-glucose, cyclic 4,4',5,5',6,6'-hexahydroxy[1,1'-biphenyl]-2,2'-dicarboxylate; D-glucose, cyclic 4,6-(4,4',5,5',6,6'-hexahydroxy[1,1'-biphenyl]-2,2'-dicarboxylate); D-glucose, cyclic mono(4,4',5,5',6,6'-hexahydroxy[1,1'-biphenyl]-2,2'-dicarboxylate); D-glucopyranose, cyclic 2,3-(4,4',5,5',6,6'-hexahydroxy[1,1'-biphenyl]-2,2'-dicarboxylate); D-glucopyranose, cyclic 4,6-(4,4',5,5',6,6'-hexahydroxy[1,1'-biphenyl]-2,2'-dicarboxylate); D-glucopyranose, cyclic mono(4,4',5,5',6,6'-hexahydroxy[1,1'-biphenyl]-2,2'-dicarboxylate); D-glucopyranose, cyclic 4,6-(4,4',5,5',6,6'-hexahydroxydiphenate); glucopyranose, cyclic ester with (6-carboxy-2,4-dihydroxy-3-oxo-1,4-cyclohexadien-1-yl) gallic acid; 4,7-methanodibenzo[th][1,4]dioxecin-5,10-dione; 7,8-dihydro-1,2,3,12,13,14,15-heptahydroxy-8-(1,2,3-trihydroxypropyl); stereoisomers thereof, or combinations thereof.

Also included in the invention are enzymes and genes encoding enzymes involved in the synthesis of the compounds described above. Non-limiting examples of enzymes that may be involved in synthesis include beta-glucosidase, biopectinase, catechol-O-methyl transferase, chalcone synthase, chalcone synthase/chalcone isomerase, cinnamoyl esterase, cyclomaltodextrin glucanyltransferase, dihydroflavonol 4-reductase, flavanone 3-hydroxylase, flavonol synthase, flavonoid 3-O-glucosyltransferase, flavonoid 7-O-glucosyltransferase, glucansucrase, glycosidase, glycoside hydroxylases, glycosyltransferases, glycosynthases, peroxidase, phenolase, phenylalanine ammonia lyase, polygalacturonase, polyphenol oxidase, rhamnosidase, stilbene synthase, shikimate pathway enzymes, wheat germ enzyme, and so forth.

The concentration of the polyphenolic compounds in the composition can and will vary depending on the type of anti-biofilm and whether the compound is provided alone or in combination with another compound. In general, the concentration may range from about 0.0005 mg/mL to about 0.5 mg/mL. In various embodiments, the concentration may range from about 0.0005 mg/mL to about 0.005 mg/mL, from about 0.005 mg/mL to about 0.05 mg/mL, or from about 0.05 mg/mL to about 0.5 mg/mL. Typically, the concentration in the composition is sub-inhibitory for growth of the microorganisms of interest. That is, the concentration of the compound in the composition is less than the concentration that reduces the growth of the microorganisms to a level of about 50% of a corresponding population of untreated microorganisms. In another embodiment, the concentration of the compound in the composition is less than the concentration that reduces the growth of the microorganisms to a level of about 90% of a corresponding population of untreated microorganisms.

(e) Optional Excipient(s)

In some embodiments, the composition of the invention may further comprise at least one pharmaceutically acceptable excipient. Non-limiting examples of suitable excipients include diluents, binders, fillers, buffering agents, pH modifying agents, disintegrants, dispersing agents, stabilizers, preservatives, and coloring agents. The amount and types of excipients may be selected according to known principles of pharmaceutical science.

In one embodiment, the excipient may include at least one diluent. Non-limiting examples of suitable diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lacitol, mannitol, malitol, sorbitol, xylitol, maltodextrin, and trehalose.

In another embodiment, the excipient may comprise a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof.

In another embodiment, the excipient may include a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may comprise a buffering agent. Representative examples of suitable buffering agents include, but are not limited to, MOPS, HEPES, TAPS, Bicine, Tricine, TES, PIPES, MES, Tris buffers or buffered saline salts (e.g., Tris buffered saline or phosphate buffered saline).

In various embodiments, the excipient may include a pH modifier. By way of non-limiting example, the pH modifying agent may be sodium carbonate or sodium bicarbonate.

In another alternate embodiment, the excipient may also include a preservative. Non-limiting examples of suitable preservatives include antioxidants, such as alpha-tocopherol or ascorbate.

In a further embodiment, the excipient may include a disintegrant. Suitable disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth.

In yet another embodiment, the excipient may include a dispersion enhancer. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In a further embodiment, the excipient may include a lubricant. Non-limiting examples of suitable lubricants include minerals such as talc or silica; and fats such as vegetable stearin, magnesium stearate or stearic acid.

In still another embodiment, it may be desirable to provide a coloring agent. Suitable color additives include, but are not limited to, food, drug and cosmetic colors (FD&C), drug and cosmetic colors (D&C), or external drug and cosmetic colors (Ext. D&C).

The weight fraction of the excipient(s) in the composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

(II) Synergistic Combinations

In some aspects, a combination comprising at least one phenolic phytochemical and at least one antimicrobial agent is provided. The combination of the at least one phenolic phytochemical and the at least one antimicrobial is synergistic in that the combination is more effective than the additive results of either component of the combination.

(a) Phenolic Phytochemical(s)

The combination comprises at least one phenolic phytochemical. The term "phytochemical" refers to a chemical compound that occurs naturally in plants. In some aspects, the phenolic phytochemical(s) may be the composition described in section (I) or may be present in the composition described in section (I). In other aspects, the phenolic phytochemical in the combination may be chosen from caffeic acid, 3-caffeoylquinic acid, 4-caffeoylquinic acid, 5-caffeoylquinic acid, corosine, 1,4-dicaffeoylquinic acid, ellagic acid, euscaphic acid, euscaphic acid-28-glucoside, ferulic acid, gallic acid, kaempferol, kaempferol-3-O-(6"-p-coumaroyl)-β-D-glucopyranoside, kaempferol-3-O-α-L-arabinopyranoside, kaempferol-3-O-(6"-feruloyl)-β-D-glucopyranoside, kaempferol-3-O-β-D-galactoside, kaempferol-3-O-glucuronide, kaempferol-3-O-β-D-glucuronide, kaempferol-3-O-β-D-glucoside, luteolin-7-O-β-D-glucuronide, nigaichigoside, oleanolic acid, quercetin, quercetin-3-O-β-D-glucuronide, quercetin-3-O-β-D-glucoside, quercetin-3-O-α-L-rhamnoside, quercetin-3-O-glucuronide, rubanthrone A, rubanthrone B, rubanthrone C, tiliroside, tormentic acid, 23-hydroxy tormentic acid, tormentic acid-28-glucoside, ursolic acid, 2α-hydroxyursolic acid, ursolic acid-28-glucoside, and combinations thereof.

In preferred embodiments, the phenolic phytochemical of the combination may be chosen from ellagic acid, ellagic acid derivatives (such as ellagic acid xylopyranoside, ellagic acid xylofuranoside, ellagic acid mannopyranoside, and ellagic acid rhamnoside), sapogenins, and combinations thereof.

The concentration of the phenolic phytochemical in the combination can and will vary depending upon the identity of the phytochemical and the use of the combination. See section (I)(d) above.

(b) Antimicrobial Agent(s)

The combination also comprises at least one antimicrobial agent. A variety of antimicrobial agents may be included in the combination of the invention. For example, the antimicrobial agent may be antibiotic, an antifungal agent, an antiseptic, or a combination thereof.

In some embodiments, the antimicrobial agent may be an antibiotic. Non-limiting examples of suitable antibiotics include amino glycosides (such as, e.g., amikacin, gentamicin, kanamycin, neomycin, netilmicin, streptomycin, and tobramycin); beta-lactams (i.e., penicillins such as amoxicillin, ampicillin, carbenicillin, cloxacillin, dicloxacillin, nafcillin, oxacillin, penicillin G, penicillin V, piperacillin, and ticarcillin; cephalosporins such as cefadroxil cefazolin, cephalexin, cefaclor, cefamandole, cephalexin, cefoxitin, cefprozil, cefuroxime, cefixime, cefdinir, cefditoren, cefoperazone, cefotaxime, cefpodoxime, ceftazidime, ceftibuten, ceftizoxime, and ceftriaxone; carbecephems such as loracarbef; carbapenems such as certapenem, imipenem, and meropenem); glycopeptides (such as vancomycin, ramoplanin, teicoplanin, telavancin, bleomycin, ramoplanin, and decaplanin); macroglides (such as azithromycin, clarithromycin, dirithromycin, erythromycin, and troleandomycin; monobactam); polypeptides (such as actinomycin, bacitracin, colistin, and polymyxin B); quinolines (such as, ciprofloxacin, enoxacin, gatifloxacin, levofloxacin, lomefloxacin, moxifloxacin, norfloxacin, ofloxacin, and trovafloxacin); sulfonamides (such as co-trimoxazole, mafenide, sulfacetamide, sulfamethizole, sulfasalazine, sulfisoxazole, trimethoprim, and trimethoprim-sulfamethoxazole); tetracyclines (such as demeclocycline, doxycycline, minocycline, oxytetracycline, and tetracycline); and other antibiotics (e.g., rifamycins such as rifampin; lincosamides such as clindamycin and lincomycin; lipopeptides such as daptomycin; phenolics such as triclosan). In preferred embodiments, the antibiotic may be amphotericin B, clindamycin, daptomycin, dicloxicillin, minocycline, nafcillin, oxacillin, ramoplanin, rifampin, triclosan, vancomycin, or combinations thereof. In exemplary embodiments, the antibiotic may be clindamycin, daptomycin, oxacillin, or vancomycin.

In other embodiments, the antimicrobial agent may be an antifungal agent. Suitable antifungal agents include, without limit, allylamines (such as amorolfine, butenafine, naftifine, and terbinafine); antimetabolites (such as flucytosine); azoles (such as bifonazole, clotrimazole, econazole, fluconazole, itraconazole, ketoconazole, miconazole, ravuconazole, posaconazole, terconazole, and voriconazole); echinocandins (such as caspofungin, micafungin, and anidulafungin); mitotic inhibitors (such as griseofulvin); phenolics (such as triclosan); and polyenes (such as Amphotericin B, candicin, filipin, hamycin, natamycin, nystatin, and rimocidin). Preferred antifungal agents include Amphotericin B, fluconazole, griseofulvin, triclosan, and combinations thereof.

In additional embodiments, the antimicrobial agent may be an antiseptic agent. Non-limiting examples of suitable antiseptic agents include biguanides (such as alexidine, chlorhexidine, polyhexamethylbiguanide); dyes (such as genetian violet, methyl violet, methylene blue); metal ion salts or conjugates thereof (such as silver, silver sulfadiazine, zinc, copper, bismuth, gallium, iodine); phenolics (such as chloroxylenol, hexachlorophene, iodophene, triclosan, and thymol); and quaternary ammonium compounds (such as benzalkonium chloride (also called alkyldimethylbenzylammonium chloride), benzethonium chloride, cetalkonium chloride, cetylpyridinium chloride, cetrimonium, cetrimide, didecyldimethylammonium chloride, dofanium chloride, domiphen bromide, methylbenzethonium chloride, tetraethylammonium bromide, and 3-(trimethyoxysilyl)-propyl dimethyloctadecyl ammonium chloride). Preferred antiseptics include benzalkonium chloride, chlorhexidine, silver oxide, silver sulfadiazine, and combinations thereof.

The concentration of the antimicrobial agent can and will vary depending upon the identity of the agent and the use of the combination. The concentration of the antimicrobial agent may range from very low levels (e.g., microorganism growth is not reduced to a substantial degree) to very high levels (i.e., it may exceed by 2- to 1000-fold the concentration of the agent that eradicates an equivalent free-floating population of the same microorganisms).

(c) Optional Excipient(s)

In some embodiments, the combination of the invention may optionally comprise at least one pharmaceutically acceptable excipient. Non-limiting examples of suitable excipients are detailed above in section (I)(e).

The weight fraction of the excipient(s) in the combination may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the combination.

(d) Preferred Synergistic Combinations

Some preferred combinations may comprise a phenolic-rich fraction derived from a plant as detailed in section (I) and either clindamycin, daptomycin, dicloxcillin, minocycline, oxacillin, ramoplanin, rifambin, triclosan, or vancomycin. Other preferred combinations may comprise a mixture of ellagic acid and/or ellagic acid derivatives and either clindamycin, daptomycin, dicloxcillin, minocycline, oxacillin, ramoplanin, rifambin, triclosan, or vancomycin.

(III) Method for Inhibiting Formation of a Biofilm

Another aspect of the invention encompasses a method for inhibiting formation of a biofilm. The method comprises contacting a plurality of free floating microorganisms with a polyphenolic composition provided in section (I) or a fraction thereof such that formation of a biofilm is inhibited. The type of microorganism and the location of the microorganisms that are contacted with the polyphenolic compositions of the invention can and will vary. Without being bound to any particular theory, it appears that the polyphenolic compositions inhibit or interfere with biofilm formation by disrupting cell adhesion such that a weakened or patchy biofilm is formed. Thus, the method described herein may be used prophylactically to prevent formation of a biofilm.

(a) Polyphenolic Compositions

The compositions described in section (I) or fractions thereof are suitable for use in the method for inhibiting biofilm formation.

(b) Microorganisms

A variety of microorganisms have the ability to form biofilms. For example, biofilms may be formed by bacteria, archaea, fungi, protozoa, algae, and combinations thereof. Non-limiting examples of bacteria that may form biofilms include *Staphylococcus, Streptococcus, Peptostreptococcus, Corynebacterium, Clostridium, Listeria, Bacillus, Enterobacteriaceae, Pseudomonas, Moraxella, Helicobacter, Stenotrophomonas, Bdellovibrio,* and *Legionella*. Fungi that may form biofilms include, without limit, *Candida*. In various embodiments, the biofilm may comprise bacteria such as be *Corynebacterium* spp., *Escherichia coli, Enterococcus* spp., *Klebsiella* spp., *Legionella* spp., *Neisseria gonorrhoeae, Pseudomonas aeruginosa, Staphylococcus* spp., methicillin-resistant *Staphylococcus* spp., *Streptococcus mutans,* or *Streptococcus sanguinis*. In an exemplary embodiment, the biofilm comprises *Staphylococcus aureus* or methicillin-resistant *Staphylococcus aureus*.

The location of the plurality of free floating microorganisms can and will vary. In some embodiments, the plurality of microorganisms (or biofilm) may be on a surface or within a subject (e.g., a veterinary subject, a health care patient, a health care worker, or a food production worker). For example, the microorganisms (or biobiofilm) may be on a squamous epithelial surface (e.g., skin surface), or a mucus membrane surface (e.g., nasal, respiratory, or alimentary tract surfaces). Additionally, the microorganisms (or biofilm) may be on the surface of an internal organ or tissue of the subject, within an internal organ or tissue of the subject, or systemic to the subject. Suitable subjects are detailed below. In other embodiments, the microorganisms (or biofilm) may be on a surface of an implanted medical device. Suitable medical devices are detailed below. In still further embodiments, the microorganisms (or biofilm) may be on or within a food product, or a piece of equipment used in the preparation of the food product, as detailed below.

(i) Subjects

In some embodiments, the microorganisms (or biofilm) may be on a surface or within the body of a subject. For example, the subject may be a veterinary subject. Non-limiting examples of suitable veterinary subjects include companion animals such as cats, dogs, rabbits, horses, and rodents such as gerbils; agricultural animals such as cows, cattle, pigs, goats, sheep, horses, deer, chickens and other fowl; zoo animals such as primates, elephants, zebras, large cats, bears, and the like; and research animals such as rabbits, sheep, pigs, dogs, primates, mice, rats and other rodents. For instance, the composition may be used to treat skin infections, soft tissue infections, and/or mastitis in veterinary subjects such as companion animals and/or agricultural animals. The veterinary subject may be suffering from or diagnosed with a condition needing treatment, or the veterinary subject may be treated prophylactically.

In other embodiments, the subject may be a human health care patient. Non-limiting examples of suitable health care patients include ambulatory patients, surgery patients, medical implantation patients, hospitalized patients, long-term care patients, nursing home patients, and the like. In still other embodiments, the subject may be a health care worker. Suitable health care workers include those with direct and indirect access to patients, medical equipment, medical facilities, and the like.

In still other embodiments, the subject may be a food production worker. A food production worker encompasses any individual with access to fresh or processed food products. Non-limiting examples include restaurant workers, food preparers, food processing workers, food plant workers, farm workers, and so forth.

In some embodiments, the subject may be suffering from or diagnosed with an infection or disease state in which treatment with the composition will inhibit or prevent biofilm formation. In other embodiments, the subject may be treated prophylactically with the composition such that biofilm formation will be inhibited or prevented.

(ii) Medical Devices

In other embodiments, the plurality of microorganisms may be on a surface of an implantable medical device. For example, the implantable medical device may be a catheter. Non-limiting examples of suitable catheters include intravascular catheters (such as, e.g., arterial catheters, central venous catheters, hemodialysis catheters, peripheral and venous catheters), endovascular catheter microcoils, peritoneal dialysis catheters, urethral catheters, and catheter access ports. In another embodiment, the implantable device may be a cardiac device. Suitable cardiac devices include, without limit, cardiac stents, defribrillators, heart valves, heart ventricular assist devices, OEM component devices, pacemakers, and pacemaker wire leads. In a further embodiment, the implantable medical device may be an orthopedic device. Non-limiting examples of suitable orthopedic devices include knee replacements, hip replacements, other joint replacements, spinal disc replacements, orthopedic pins, plates, screws, rods, and orthopedic OEM components. In yet other embodiments, suitable implantable medical devices include endotracheal tubes, nasogastric feeding tubes, gastric feeding tubes, synthetic bone grafts, bone cement, biosynthetic substitute skin, vascular grafts, surgical hernia mesh, embolic filter, ureter renal biliary stents, urethral slings, gastric bypass balloons, gastric pacemakers, insulin pumps, neurostimulators, penile implants, soft tissue silicone implants, intrauterine contraceptive devices, cochlear implants, and voice restoration devices.

(iii) Food Products

In additional embodiments, the plurality of microorganisms may on a surface or within a food product, or a piece of equipment used in the preparation of the food product. Non-limiting examples of suitable food products include fresh or processed food. The food may be fresh, frozen, canned, dried, baked, fried, processed, fruit or fruit-based, vegetable or vegetable-based, grain or grain-based, cereal or cereal-based, nut or nut-based, dairy or dairy-based, egg or egg-based, meat or meat-based, seafood or seafood-based, algae or algae-based, and so forth. Also included is any piece of equipment used in the preparation of a food product. Non-limiting examples of suitable equipment include washers, dryers, blenders, grinders, mixers, homogenizers, extruders, and the like.

(c) Contacting the Free Floating Microorganisms

The method comprises contacting the plurality of free floating microorganisms with a polyphenolic composition described in section (I) or a fraction of the polyphenolic composition described in section (I). In embodiments in which the plurality of microorganisms is on or within a subject, the contacting step may comprise administering a preparation comprising the polyphenolic composition orally, topically (i.e., transdermally or transmucosally), or parenterally (e.g., subcutaneously, intradermally, intravenously, intramuscularly, or intraperitoneally).

Preparations for oral administration generally contain inert excipients in addition to the active pharmaceutical ingredient. Oral preparations may be enclosed in gelatin capsules or compressed into tablets. Common excipients used in such preparations include pharmaceutically compatible fillers/diluents such as microcrystalline cellulose, hydroxypropyl methylcellulose, starch, lactose, sucrose, glucose, mannitol, sorbitol, dibasic calcium phosphate, or calcium carbonate; binding agents such as alginic acid, carboxymethylcellulose, microcrystalline cellulose, gelatin, gum tragacanth, or polyvinylpyrrolidone; disintegrating agents such as alginic acid, cellulose, starch, or polyvinylpyrrolidone; lubricants such as calcium stearate, magnesium stearate, talc, silica, or sodium stearyl fumarate; glidants such as colloidal silicon dioxide; sweetening agents such as sucrose or saccharin; flavoring agents such as peppermint, methyl salicylate, or citrus flavoring; coloring agents; and preservatives such as antioxidants (e.g., vitamin A, vitamin C, vitamin E, or retinyl palmitate), citric acid, or sodium citrate. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For topical (e.g., transdermal or transmucosal) administration, penetrants appropriate to the barrier to be permeated are generally included in the preparation. Transmucosal administration may be accomplished through the use of nasal sprays, aerosol sprays, tablets, or suppositories, and transdermal administration may be via ointments, salves, gels, patches, or creams as generally known in the art.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

Additionally, the contacting step may comprise rinsing, cleaning, flushing, etc. the skin surface of a subject with a preparation comprising the polyphenolic composition. In further embodiments, the contacting step may comprise a surgical or antiseptic lavage, wherein a body cavity, organ, or tissue of a surgical subject is flushed, rinsed, or sprayed with a preparation comprising the polyphenolic composition.

In other embodiments in which the plurality of microorganisms is one a surface of an object (e.g., medical device, food product, or food preparation equipment), the contacting step may comprise coating the surface(s) of the object with a preparation comprising the polyphenolic composition, wherein the polyphenolic composition elutes from the coating over a period of time. The coating that covers the object may comprise a hydrogel (i.e., a gel comprising water soluble polymers) such that the elution of the polyphenolic composition occurs over an extended period of time. The period of time during which composition elutes from the coating and contacts the plurality of free floating microorganisms may range from about several days to more than several months. In other embodiments, the contacting step may comprise rinsing, dipping, spraying, etc. the surface(s) of the object with a preparation comprising the polyphenolic composition.

In general, contact with the polyphenolic compositions inhibits or retards formation of a biofilm. Those of skill in the art are familiar with techniques for assessing the presence of a biofilm. For example, as detailed in Example 3, a biofilm may be assessed by staining with a dye such as crystal violet, whereas the free floating cells of the same organism(s) are not stained with the dye. Biofilm formation may be inhibited in an amount ranging from about 1% to about 99% relative to that of untreated control microorganisms. Biofilm formation may be inhibited by at least about 10%, at least about 20%, at least about 30%, at least about 40%, at least about 50%, at least about 60%, at least about 70%, at least about 80%, at least about 90%, or at least about 99% as compared to corresponding microorganisms not contacted with the polyphenolic composition. In preferred embodiments, biofilm formation may be inhibited at least 50% relative to untreated control microorganisms. In exemplary embodiment, biofilm formation may be inhibited by at least 90% relative to untreated control microorganisms.

(IV) Method for Reducing Growth of an Established Biofilm

Another aspect of the invention encompasses a method for inhibiting growth of an established biofilm. The method comprises contacting the biofilm with the combinations described in section (II) such that the number of microorganisms in the biofilm is reduced. In general, contact with a combination comprising a phenolic phytochemical(s) and an antimicrobial agent(s) is synergistic in that the degree of inhibition of microbial growth is more than additive of the activity of either the phytochemical(s) or the antimicrobial agent(s) alone.

Examples of suitable microorganisms that are able to form biofilms are detailed above in section (III)(b).

(a) Combinations

Suitable combinations for use in the method are detailed in section (II) above. In some preferred embodiments, the combination may comprise at least one polyphenol composition derived from a plant as detailed in section (I) and at least one antimicrobial agent. In other preferred embodiments, the combination may comprise a mixture of ellagic acid and/or at least one glycosylated derivative of ellagic acid, and at least one antimicrobial agent.

(b) Contacting the Biofilm

The method comprises contacting the biofilm with the combination detailed in section (II). The biofilm may be present on a surface or within a subject as detailed above in section (III)(b)(i), a medical device as detailed in section (III)(b)(ii), or a food product/food preparation equipment as detailed in section (III)(b)(iii).

Means for contacting the subject or object of interest are detailed above in section (III)(c).

The biofilm may be contacted with the components of the combination simultaneously, that is as a single preparation. Alternatively, the biofilm may be contacted with the components of the combination sequentially. For example, the biofilm may be contacted with the phenolic phytochemical(s) then contacted with the antimicrobial agent(s). Alternatively, the biofilm may be contacted first with the antimicrobial agent(s) and then contacted with the phenolic phytochemical(s).

The duration of contact between the biofilm and the combinations described in section (II) can and will vary. In various embodiments, the duration of contact may range from several days to more than several months. For example, the duration of contact may be about 3 days, about 7 days, about 14 days, about 21 days, about 1 month, about 3 months, or longer than 3 months.

Contact with the combinations described in section (II) inhibits biofilm growth by reducing the number of microorganisms in the biofilm. In some aspects of the invention, the number of microorganisms is reduced in an amount ranging from 1% to 99% compared to untreated control microorganisms. In some aspects of the invention, the number of microorganisms may be reduced by at least about 10%, at least about 20%, at least about 30%, at least about 40%, at least about 50%, at least about 60%, at least about 70%, at least about 80%, at least about 90%, or at least about 99% as compared to corresponding microorganisms not contacted with the combination comprising the phenolic phytochemical and the antimicrobial agent.

Figure 9:
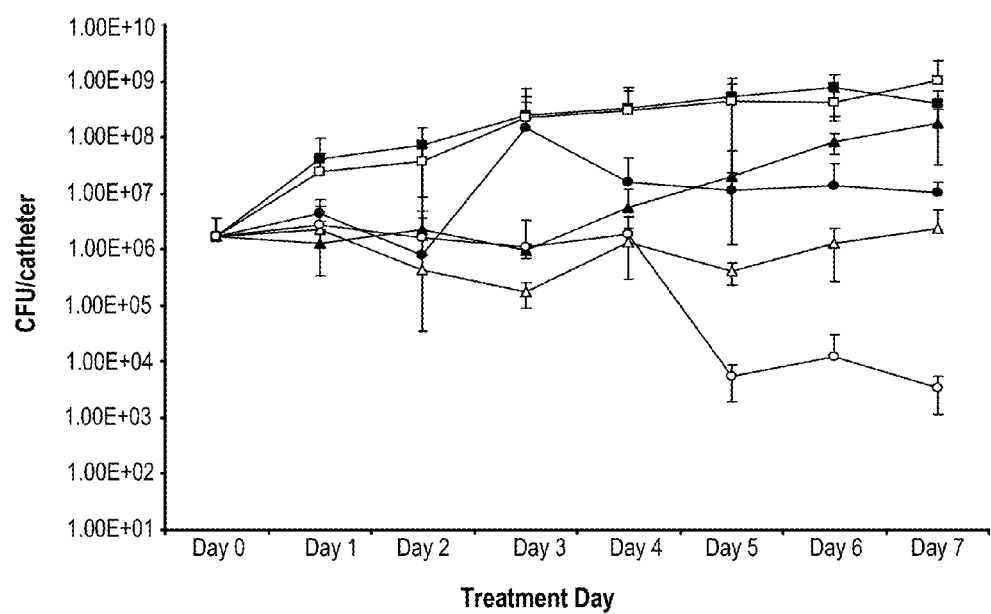
FIG. 9 illustrates synergistic activity of fraction 220D-F2 and an antibiotic on disrupting established biofilms. (A) daptomycin, (B) clindamycin, (C) vancomycin, (D) oxacillin. Solid squares: biofilm control (no treatment); open squares: extract control (200 mg/L 220D-F2); solid triangles: antibiotic at 1× the breakpoint MIC; open triangles: antibiotic at 1× the breakpoint MIC+200 mg/L 220D-F2; solid circles: antibiotic at 10× the breakpoint MIC; open circles: antibiotic at 10× the breakpoint MIC+200 mg/L 220D-F2.
Figure 9:
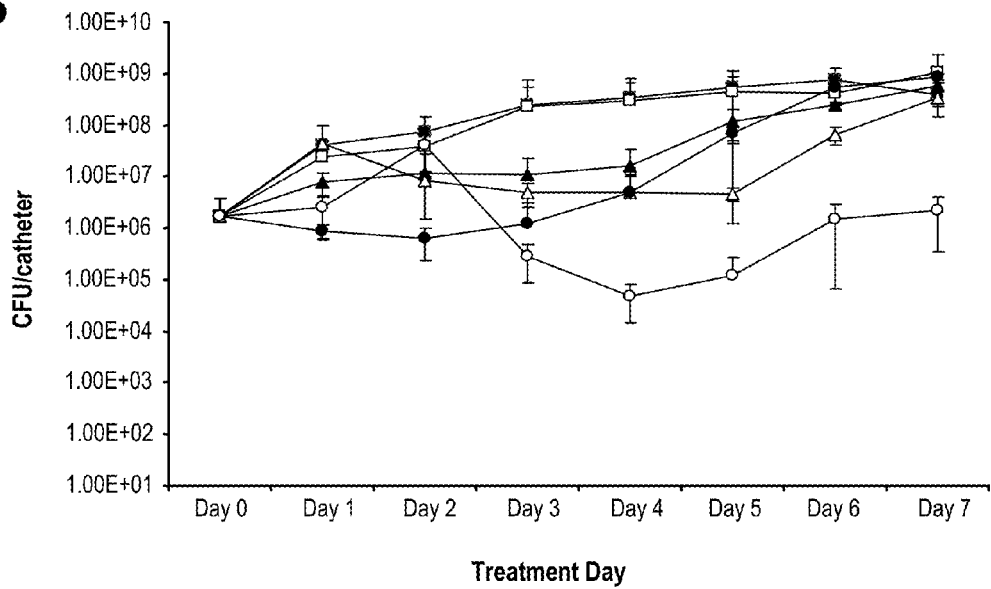
Figure 9:
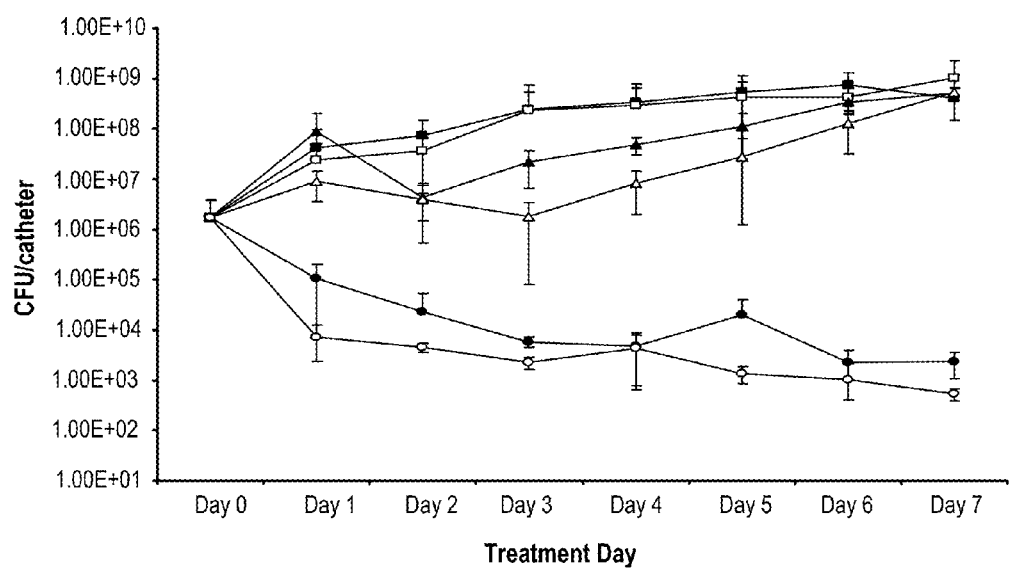
Figure 9:
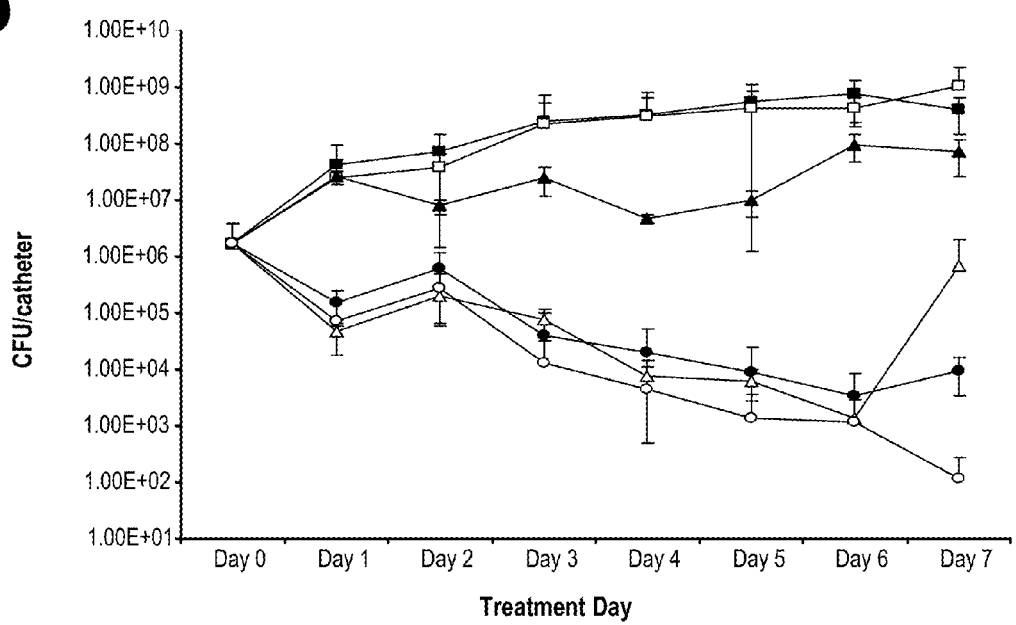

Moreover, the activity of the combinations may be greater than the sum of the activities of either component alone. For example, FIG. 9 compares the number of viable cells when the biofilm is contacted with an antimicrobial alone, the phenolic phytochemical alone, and the combination of the antimicrobial and the phenolic phytochemical.

In some embodiments, the combination of the phenolic phytochemical and the antimicrobial reduces the number of viable cells by an amount of about 1 to about 10 log units above the antimicrobial alone. In other embodiments, the combination reduces the number of viable cells by about 2 log units above the antimicrobial alone, or by about 4 log units above the antimicrobial alone, or by about 6 log units above the antimicrobial alone, or by about 8 log units above the antimicrobial alone, or about 10 log units above the antimicrobial alone. In preferred embodiments, the combination reduces the number of viable cells by about 5 log units over the antimicrobial alone.

In another aspect, the combination reduces the number of viable cells by an amount of about 1 to about 10 log units above the phenolic phytochemical alone. In other embodiments, the combination reduces the number of viable cells by about 2 log units above the phenolic phytochemical alone, or by about 4 log units above the phenolic phytochemical alone, or by about 6 log units above the phenolic phytochemical alone, or by about 8 log units above the phytochemical alone, or about 10 log units above the phenolic phytochemical alone. In preferred embodiments, the combination reduces the number of viable cells by about 5 log units over the phenolic phytochemical alone.

In some embodiments, contact with the combination provided in section (II) may significantly reduce the number of microorganisms about 1 to 3 days. In other embodiments, the number of microorganisms may be reduced significantly after 3 to 5 days of contact. In still other embodiments, it may take up to 5 to 7 days of contact with the combinations to reduce significantly the number of microorganisms in the biofilm. In additional embodiments, it may take longer than about 7 days of contact with the combinations to reduce significantly the number of microorganisms in the biofilm.

DEFINITIONS

To facilitate understanding of the invention, the following terms are defined.

The term "biofilm" as used herein refers to an aggregate of microorganisms in which cells adhere to each other and/or to a surface. These adherent cells are frequently embedded within a self-produced matrix of extracellular polymeric substance. The microorganisms comprising a biofilm may include bacteria, archaea, fungi, protozoa, algae, or combinations thereof.

The term "phenolic-rich fraction" as used herein refers to a fraction enriched in phenolic compounds and/or polyphenolic compounds and their derivatives.

The term "synergistic" as in "synergistic effect" refers to an effect in which two or more agents work in synergy to produce an effect that is more than additive of the effects of each agent independently.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are included to demonstrate preferred embodiments of the invention. It should be appreciated by those of skill in the art that the techniques disclosed in the examples represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

Example 1

Preparation of Phenolic-Rich Fraction from *Rubus Ulmifolius* Root Extract

The following example details purification of phenolic-rich fractions from an ethanol extract of *Rubus ulmifolius* roots. *R. ulmifolius* is a wild shrub belonging to the rose family that is native to the Mediterranean. Parts of the plant have traditionally been used to treat skin conditions. For example, fresh leaves are topically applied with pork fat in the treatment of skin and soft tissue infections and a decoction of the roots is used as a wash to prevent hair loss. In a recent screening study (Quave et al., 2008, Journal of Ethnopharmacology 118:418-428), crude ethanolic extracts from 104 Italian plants were assessed for their anti-biofilm potential and extracts from *R. ulmifolius* and nine other species were found to show some promise.

Acquisition of Botanical Materials.

Bulk samples of *R. ulmifolius* Schott. (Rosaceae) were collected from wild populations in August 2009 in the village of Ginestra, Italy. Procedures from the 2003 WHO Guidelines on Good Agricultural and Collection Practices for Medicinal Plants were followed for the collection and identification of bulk and voucher specimens. Voucher specimens (CQ-164) were deposited at the Herbarium Lucanum (HLUC) at the University della Basilicata in Potenza, Italy. The specimens were identified using the standard Italian Flora and identification was confirmed at HLUC. All soil and other contaminants (i.e. insects, other plant species etc.) were removed from each sample. Plant materials were separated by part (stems, leaves, roots, fruits), cut into small pieces, and air dried. Upon drying, materials were packed into plastic bags with silica packets and vacuum sealed. Plant materials were exported to the USA under USDA Permit PDEP-09-00228 for phytochemical evaluation and bioassays.

Isolation of Active Fraction.

Air-dried roots (1 kg) of *R. ulmifolius* were ground into a fine powder and then extracted with 95% EtOH (2×10 L) at room temperature for 72 hours with constant agitation. The filtered extracts were combined, concentrated under reduced pressure at temperatures <45° C., and lyophilized. The lyophilized extract was re-suspended in water and successively partitioned with: hexane, ethyl-acetate and butanol. The partitions were dried over anhydrous sodium sulfate, concentrated at reduced pressure, lyophilized and tested for activity. The most active partition (butanol) was subjected to column chromatography using Silica gel (0.015-0.040 µm particle size, EMD Chemicals, Gibbstown, N.J.) and fractions were collected after eluting successively with mixtures of MeOH: $CH_2Cl_2$ (30:70, 40:60, 50:50, 60:40, 70:30, 80:20, 90:10) followed by 100% MeOH and 100% $H_2O$ (18Ω purity). FIG. 1 presents a flow chart of the purification procedure. Fractions were dried, weighed and tested for activity (i.e., inhibition of biofilm formation essentially as detailed in Example 2). The 40:60 fraction (designated 220D-F2) was found to be the most active and was chosen for further study.

The active fraction (220D-F2) was characterized by liquid chromatography time of flight mass spectrometry (LC-Q/ToFMS). Separation of components was achieved on a 10 µm µBondapak C-18 column (300 mm×3.9 mm) with an isocratic mobile phase that consisted of 79% $H_2O$, 12% acetonitrile, 8% 2-propanol, and 1% formic acid. The flow rate was 1.0 ml/min. Detection was performed using a Micromass Q-ToF micro mass spectrometer (Waters/Micromass, Beverly, Mass.). The instrument was operated in the negative ion electrospray mode. The source and desolvation temperatures were set to 140 and 350° C., respectively. ESI capillary voltage was 3 kV and the cone voltage was 35 V. The collision energy was set to 5 eV. Phosphoric acid (0.1%) in acetonitrile/methanol (50/50) was used for mass calibration and as the lock-mass. The instrument was calibrated over a limited range (m/z 80-1000).

Bacterial Strains and Growth Conditions.

*Staphylococcus aureus* strains are listed in TABLE 1. Strains were grown at 37° C. in cation-adjusted Mueller-Hinton broth (CAMHB) for minimum inhibitory concentration (MIC) and minimum bactericidal concentration (MBC) assays and in tryptic soy broth (TSB) supplemented with 3.0% NaCl and 0.25% dextrose (biofilm medium, BM) for biofilm assays. For all assays, overnight cultures grown in the appropriate medium were used to inoculate fresh medium at an initial cell density of $5\times10^5$ colony-forming units (CFU) per ml. Cell density was confirmed by colony count of aliquots taken immediately following inoculation of the test strain. Test strains included primary clinical isolates and, when available, isogenic mutants in which the staphylococcal accessory regulator (sarA) had been inactivated as previously described (Beenken et al. 2010, PLoS ONE, 5:e10790).

Determination of MIC and MBC.

The MIC and MBC of the active fraction (220D-F2) were determined following Clinical and Laboratory Standards Institute (CSLI) broth microdilution methods. Briefly, test strains were inoculated into 0.1 ml CAMHB containing 220D-F2 at concentrations ranging from 0.138-4 mg/ml (0.138-4% excipient in solution). For the MIC, optical density ($OD_{600}$) was assessed immediately after inoculation and again after 18 hrs using a Biotek Synergy II microplate reader. Corrections for extract color, which can alter the OD output, were done as previously described (Quave et al., 2008, supra). The MIC was defined as the lowest concentration which inhibited growth to a level ≥90% (for $MIC_{90}$) or ≥50% (for $MIC_{50}$) than that observed with the untreated control. The MBC was determined by taking colony counts of aliquots taken from each well after 24 hrs and it was defined as the lowest concentration at which the initial density of viable cells was reduced by ≥90% (for $MBC_{90}$) or ≥50% (for $MBC_{50}$) by comparison to the untreated control. In addition, the impact of a sub-MIC dose (0.2 mg/ml) of 220D-F2 on the growth of UAMS-1 was assessed by taking cell counts at different time-intervals after inoculation and comparing these to the cell counts obtained with both UAMS-1 and its isogenic sarA mutant (UAMS-929) in the absence of exposure to 220D-F2. For these experiments, 10 ml cultures were grown at 37° C. in 25 ml Erlenmeyer flasks in BM with constant shaking (200 rpm).

Assessment of Biofilm Formation.

Biofilm formation was assessed using a microtiter plate assay as previously described (Beenken et al., 2003, Infection and Immunity 71:4206-11) except that 2-fold serial dilutions (0.0125-0.4 mg/ml, 0.0125-0.4% excipient in solution) of 220D-F2 were included in the BM. Controls for each experiment were the wild-type strain and its isogenic sarA mutant assayed in the absence of 220D-F2. The minimum biofilm inhibiting concentration (MBIC) was defined as the lowest concentration at which 220D-F2 inhibited biofilm formation to a level ≥90% (for $MBIC_{90}$) or ≥50% (for $MBIC_{50}$) than that observed with the parent strain in the absence of 220D-F2.

Confocal Laser Scanning Microscopy (CLSM) of Static Biofilms.

Two strains (UAMS-1 and the USA300 isolate UAMS-1782) and their isogenic sarA mutants (UAMS-929 and UAMS-1804) were grown in 96 well microtiter plates (Costar 3603, Corning Life Sciences) as described above. Where indicated, 220D-F2 was added to the wells at the time of inoculation. After 20 hours, the well contents were aspirated and the wells gently washed three times with 0.85% (wt/vol) NaCl. The adherent biofilm was then stained with LIVE/DEAD stain (Invitrogen) at room temperature in the dark for 18 minutes. After removal of the stain, the wells were gently washed with 0.85% NaCl before collecting CLSM images using a Zeiss LSM 510 Meta confocal scanning system and inverted microscope. SYTO 9 fluorescence was detected by excitation at 488 nm and emission collected with a 500-530 bandpass filter. All z-sections were collected at 4-μm intervals using a 10× objective lens. A 0.9×0.9 mm section of biofilm was selected from the center of the well for each image. Image acquisition and processing was performed using LSM Image Browser (Carl Zeiss). Identical acquisition settings were employed for all samples.

Statistical Analysis.

Pair-wise testing was performed based on t tests as formatted in Sigma Stat® Statistical Software Version 2 (SPSS, Inc) with P values <0.05 considered significant.

Results.

Figure 2A:
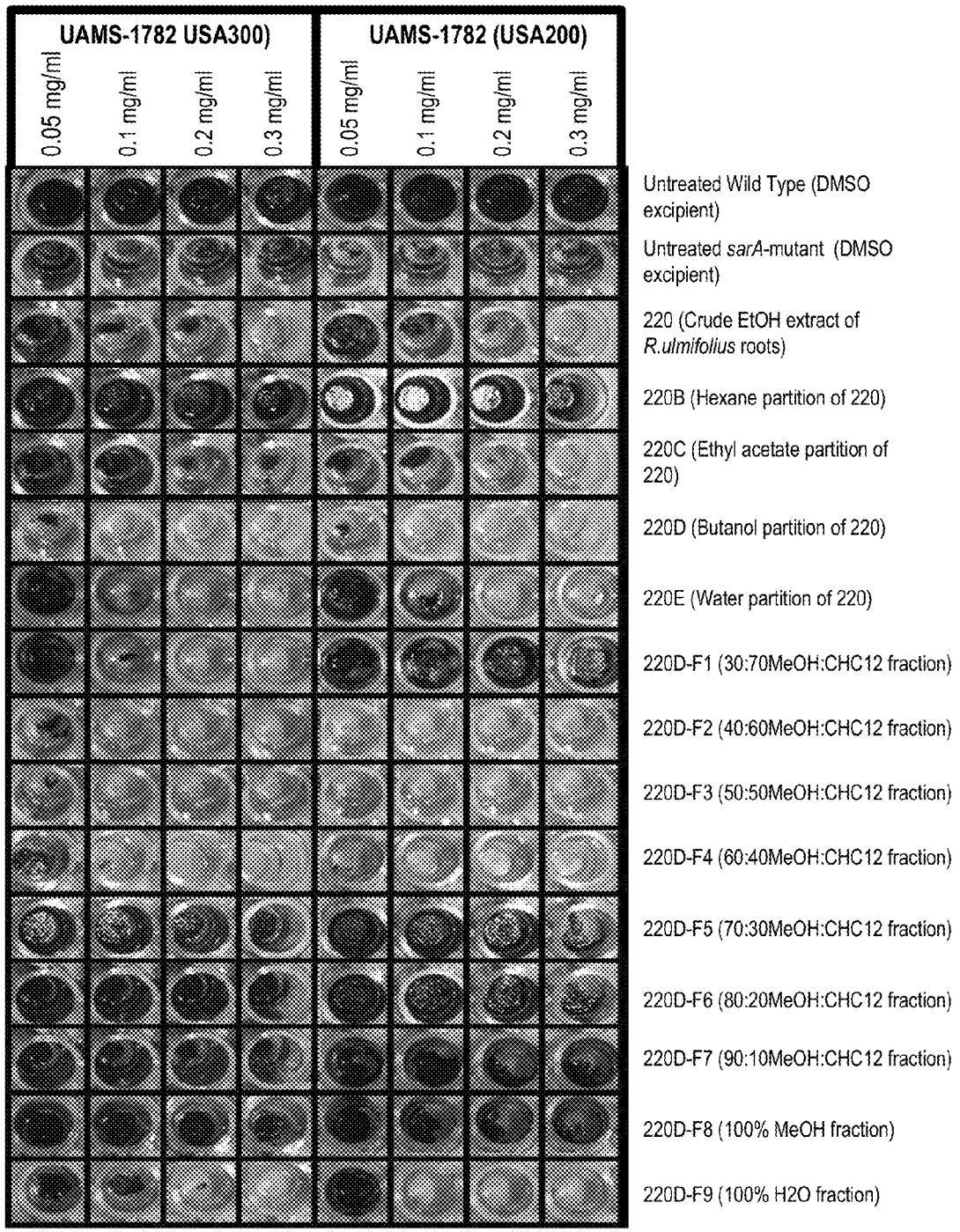
FIG. 2A illustrates the increase in biofilm-inhibiting activity of crude extract 220 during partitioning and fractionation. Shown are visual results of microtiter plate assays. Wild type (WT) strains are identified according to their UAMS I.D. on the left side and the concentration of extract added to the wells prior to inoculation is also indicated on the left. The corresponding extracts tested are indicated on the top. The untreated wild type and its respective isogenic sarA mutant are also indicated on the top. The MBICs for the crude ethanol extract, butanol partition, and 40:60, 50:50, and 60:40 MeOH:$CH_2Cl_2$ fractions were 0.2, 0.1, 0.05, 0.05 and 0.05 mg/ml, respectively, in both UAMS-1 (USA200) and UAMS-1782 (USA300) strains.
Figure 2B:
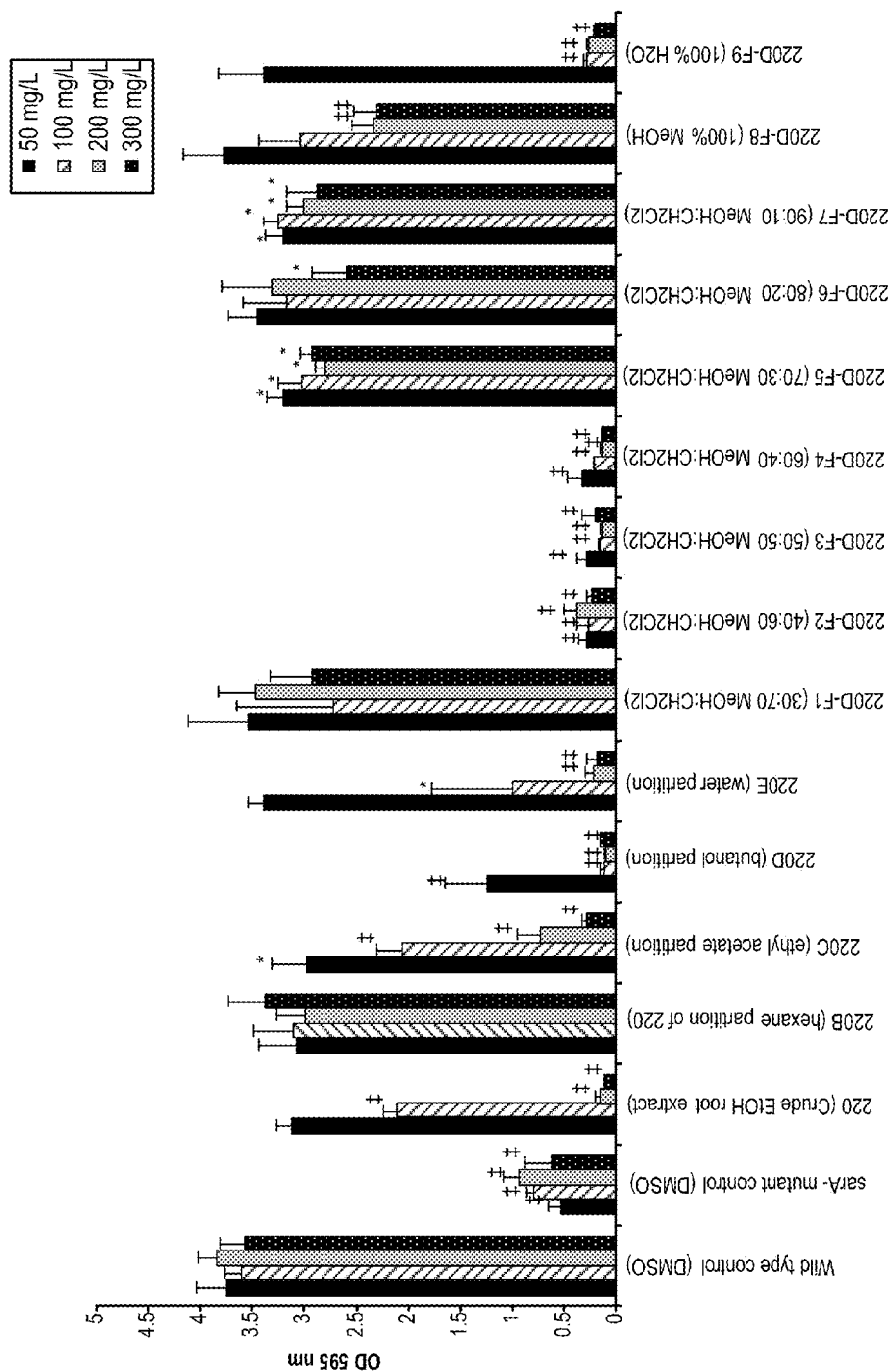
FIG. 2B presents a bar graph illustrating the dose-response relationship between the various plant fractions and UAMS-1 (USA200) cells. Some fractions exhibited levels of biofilm inhibition approximating those of the corresponding isogenic sarA mutant controls. The statistical significance of the difference between the untreated and treated wells is denoted with * ($P<0.05$) or ‡ ($P<0.001$). Both of the corresponding isogenic sarA mutants were significantly different from the wild type.
Figure 2C:
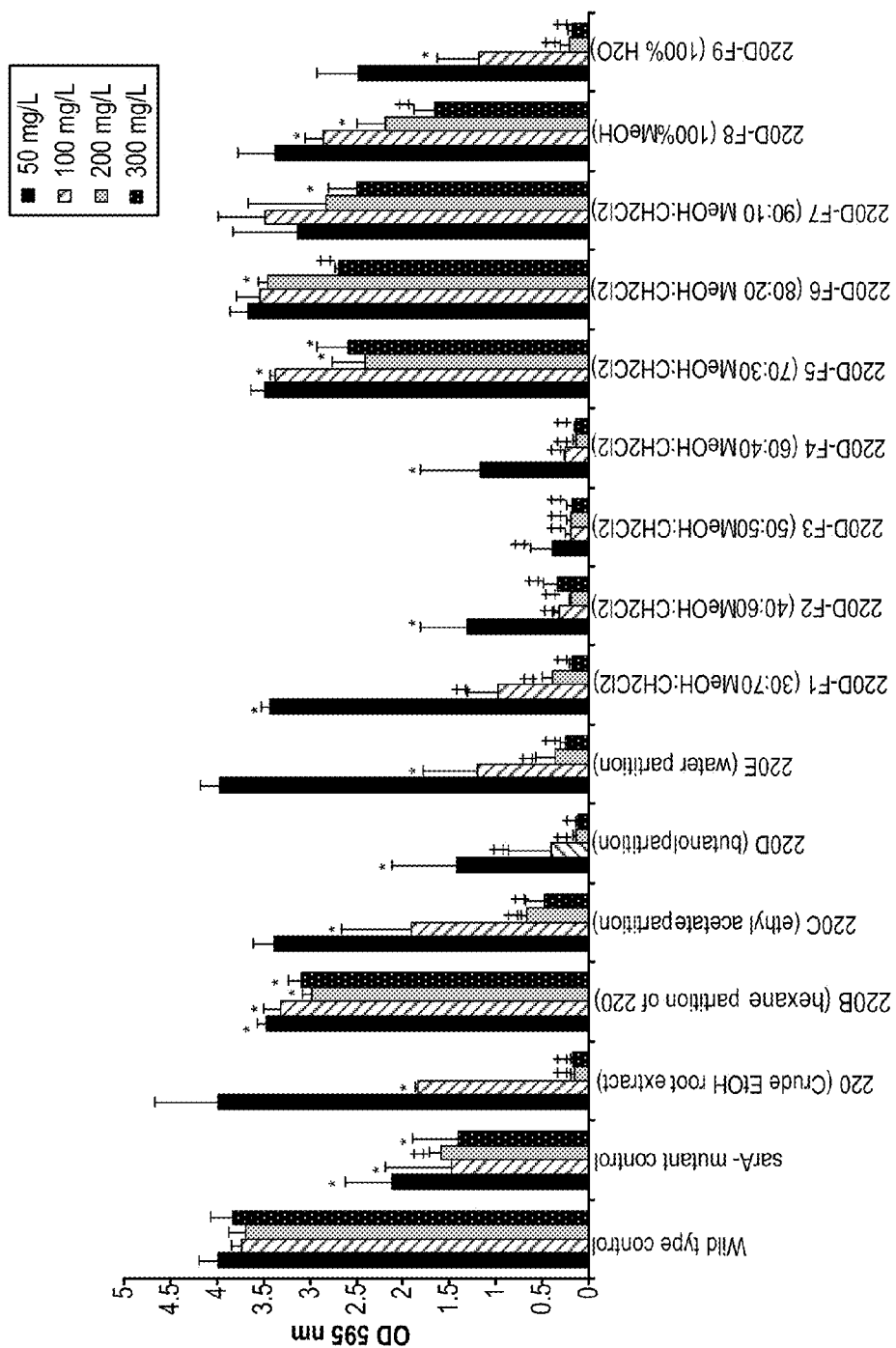
FIG. 2C presents a bar graph illustrating the dose-response relationship between the various plant fractions and UAMS-1782 (USA300) cells. Some fractions exhibited levels of biofilm inhibition approximating those of the corresponding isogenic sarA mutant controls. The statistical significance of the difference between the untreated and treated wells is denoted with * ($P<0.05$) or ‡ ($P<0.001$). Both of the corresponding isogenic sarA mutants were significantly different from the wild type.

Bioassay-guided fractionation techniques resulted in the isolation of fraction 220D-F2 from the roots of *R. ulmifolius*. The percent yield of this faction was approximately 0.329% of dry root weight. In other words, for every kilogram of root extracted, 3.29 grams of this fraction can be isolated. The potency of the extract was increased (as evidenced by lowering the total concentration necessary for inhibiting biofilm formation) following partitioning and fractionation (see FIG. 2A-C). For example, in the USA-200 isolate UAMS-1, the $MBIC_{90}$ of the crude ethanolic extract was 0.2 mg/ml. When this extract was separated by solvent partitioning techniques, the hexane partition was inactive, activity in the ethyl-acetate partition was decreased ($MBIC_{90}$: 0.3 mg/ml), activity in the butanol partition was increased ($MBIC_{90}$: 0.1 mg/ml), and activity in the water partition was unchanged ($MBIC_{90}$: 0.2 mg/ml). Thus, the most active partition (butanol) was selected for further fractionation via column chromatography. Based on separation tests with thin layer chromatography (data not shown), the solvent scheme of an increasing gradient of $MeOH:CH_2Cl_2$ was selected for fractionation of the butanol partition (refer to FIG. 1). The most activity was evident in fractions 2-4, where the $MBIC_{90}$ was 0.05 mg/ml. Little or no activity was evident in the other fractions.

Figure 3:
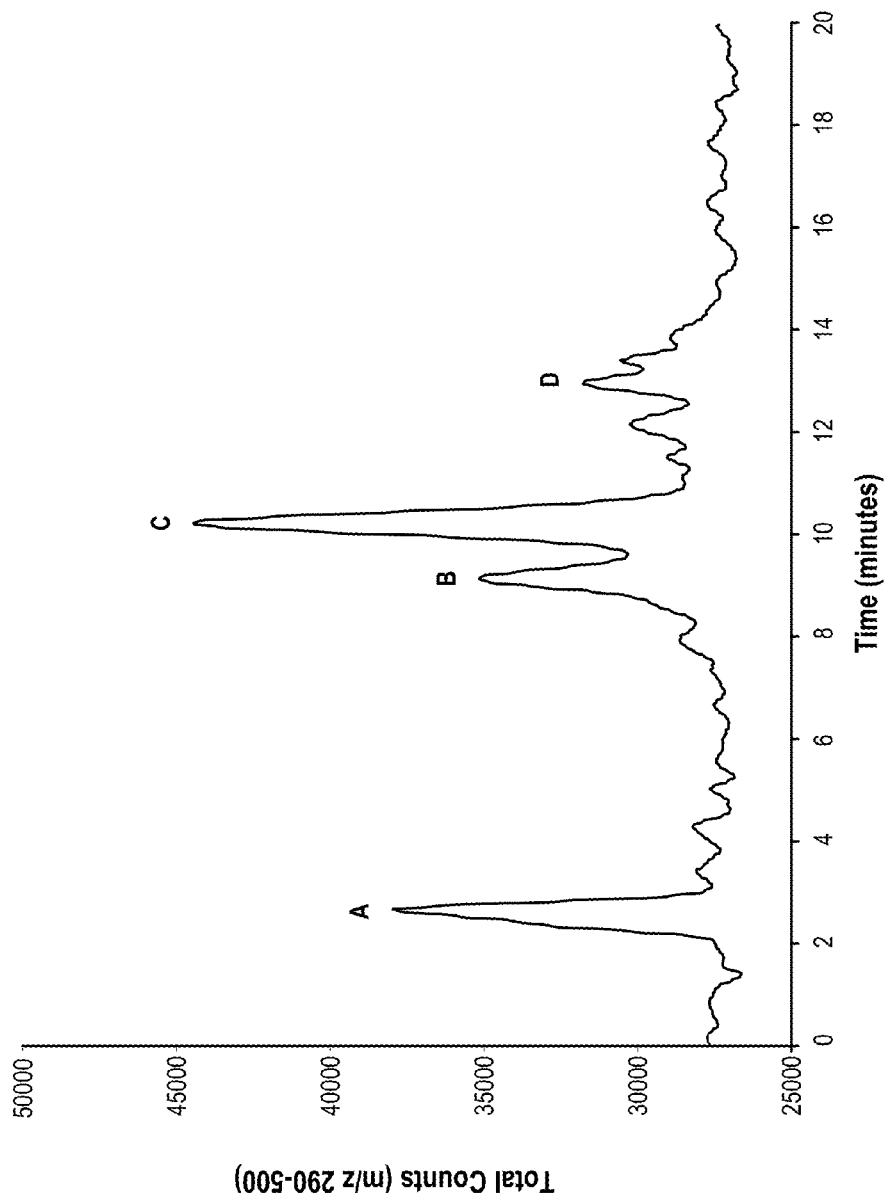
FIG. 3 presents a LC-MS chromatogram of the active fraction (220D-F2). The chromatogram was obtained using a Bondapak C-18 column LC-Q-ToF micro system. The trace represented was extracted for components in the m/z 290-500 range.

LC-Q/ToFMS yielded a chromatogram with several distinct peaks, two of which have been determined to be phenolic glycosides or derivatives thereof (FIG. 3). Peak A has been identified to have the molecular formula $C_{20}H_{18}O_{14}$. Possible compounds having this formula include D-Glucose, cyclic 3,4-[(1R)-4,4',5,5',6,6'-hexahydroxy[1,1'-biphenyl]-2,2'-dicarboxylate]; L-Ascorbic acid, 6,6'-(1,4-benzenedicarboxylate); D-Glucose, cyclic 3,6-(4,4',5,5',6,6'-hexahydroxy[1,1'-biphenyl]-2,2'-dicarboxylate), (S)—; D-Glucose, cyclic 2,3-(4,4',5,5',6,6'-hexahydroxy[1,1'-biphenyl]-2,2'-dicarboxylate), (R)—; 4,7-Methanodibenzo[th][1,4]dioxecin-5,10-dione, 7,8-dihydro-1,2,3,12,13,14,15-heptahydroxy-8-(1,2,3-trihydroxypropyl)-, stereoisomer; β-D-Glucopyranose, cyclic 2,3-(4,4',5,5',6,6'-hexahydroxy[1,1'-biphenyl]-2,2'-dicarboxylate); α-D-Glucopyranose, cyclic 2,3-(4,4',5,5',6,6'-hexahydroxy[1,1'-biphenyl]-2,2'-dicarboxylate); D-Glucose, cyclic 2,4-(4,4',5,5',6,6'-hexahydroxy[1,1'-biphenyl]-2,2'-dicarboxylate); D-Glucose, cyclic 4,6-[(1S)-4,4',5,5',6,6'-hexahydroxy[1,1'-biphenyl]-2,2'-dicarboxylate]; D-Glucose, cyclic 3,6-(4,4',5,5',6,6'-hexahydroxy[1,1'-biphenyl]-2,2'-dicarboxylate), (R)—; D-Glucose, cyclic 2,3-[(1S)-4,4',5,5',6,6'-hexahydroxy[1,1'-biphenyl]-2,2'-dicarboxylate]; D-Glucose, cyclic 3,6-(4,4',5,5',6,6'-hexahydroxy[1,1'-biphenyl]-2,2'-dicarboxylate); D-Glucose, cyclic 4,6-(4,4',5,5',6,6'-hexahydroxy[1,1'-biphenyl]-2,2'-dicarboxylate); D-Glucose, cyclic 4,4',5,5',6,6'-hexahydroxy[1,1'-biphenyl]-2,2'-dicarboxylate; D-Glucose, cyclic 2,3-(4,4',5,5',6,6'-hexahydroxy[1,1'-biphenyl]-2,2'-dicarboxylate); Glucopyranose, cyclic ester with (6-carboxy-2,4-dihydroxy-3-oxo-1,4-cyclohexadien-1-yl)gallic acid; Glucopyranose, cyclic 4,6-(4,4',5,5',6,6'-hexahydroxydiphenate), D-; β-D-Glucopyranose, cyclic 4,6-(4,4',5,5',6,6'-hexahydroxy[1,1'-biphenyl]-2,2'-dicarboxylate); D-Glucopyranose, cyclic 2,3-(4,4',5,5',6,6'-hexahydroxy[1,1'-biphenyl]-2,2'-dicarboxylate); and β-D-Glucopyranose, cyclic mono(4,4',5,5',6,6'-hexahydroxy[1,1'-biphenyl]-2,2'-dicarboxylate).

Peak C has been identified as having the molecular formula $C_{20}H_{16}O_{12}$. The peak has tentatively been identified as ellagic acid rhamnoside (i.e., [1]Benzopyrano[5,4,3-cde][1]benzopyran-5,10-dione, 2-[(6-deoxy-α-L-mannopyranosyl)oxy]-3,7,8-trihydroxy-). Other possibilities include [1]Benzopyrano[5,4,3-cde][1]benzopyran-5,10-dione, 2,3-dihydroxy-8-methoxy-7-(β-D-xylopyranosyloxy)-; 2-Butenedioic acid, 2-[(2R,3R)-3,4-dihydro-5,7-dihydroxy-3-[(3,4,5-trihydroxybenzoyl)oxy]-2H-1-benzopyran-2-yl]-, (2Z)-; [1]Benzopyrano[5,4,3-cde][1]benzopyran-5,10-dione, 2-(α-L-arabinofuranosyloxy)-3,7-dihydroxy-8-methoxy-; [1]Benzopyrano[5,4,3-cde][1]benzopyran-5,10-dione, 2,8-dihydroxy-3-methoxy-7-(β-D-xylopyranosyloxy)-; [1]Benzopyrano[5,4,3-cde][1]benzopyran-5,10-dione, 2,8-dihydroxy-3-methoxy-7-(D-xylopyranosyloxy)-; 5H,13H-Bis[1,3]dioxolo[4,5]furo[3,2-h:2',3'-s][1,4,7,11,14,17]hexaoxacycloeicosin; 5H-Benzocycloheptene-8,9- dicarboxylic acid, 2,3,4-tris(acetyloxy)-6-hydroxy-5-oxo-, 8-methyl ester; and 1,4-Naphthalenedione, 2,3,5,6,8-pentakis(acetyloxy)-. Peaks B and D gave weaker signals and possible constituents have not been identified.

Example 2

Prophylactic Anti-Biofilm Activity of Phenolic-Rich Fraction

The MIC and MDC of the active fraction 220D-F2 was determined essentially as detailed above in Example 1. The prophylactic activity of 220D-F2 to prevent biofilm formation was assessed using the microtiter plate assay essentially as described in Example 1. The prophylactic activity of this fraction was also assessed using an in vitro catheter model. For this, 1 cm catheter sections were inoculated with UAMS-1 in the presence of BM containing 220D-F2 (0.2 mg/mL). After a 24 hr incubation period in the presence of the active fraction, the catheters were processed for plate counts as described above (see Example 1).

Figure 6:
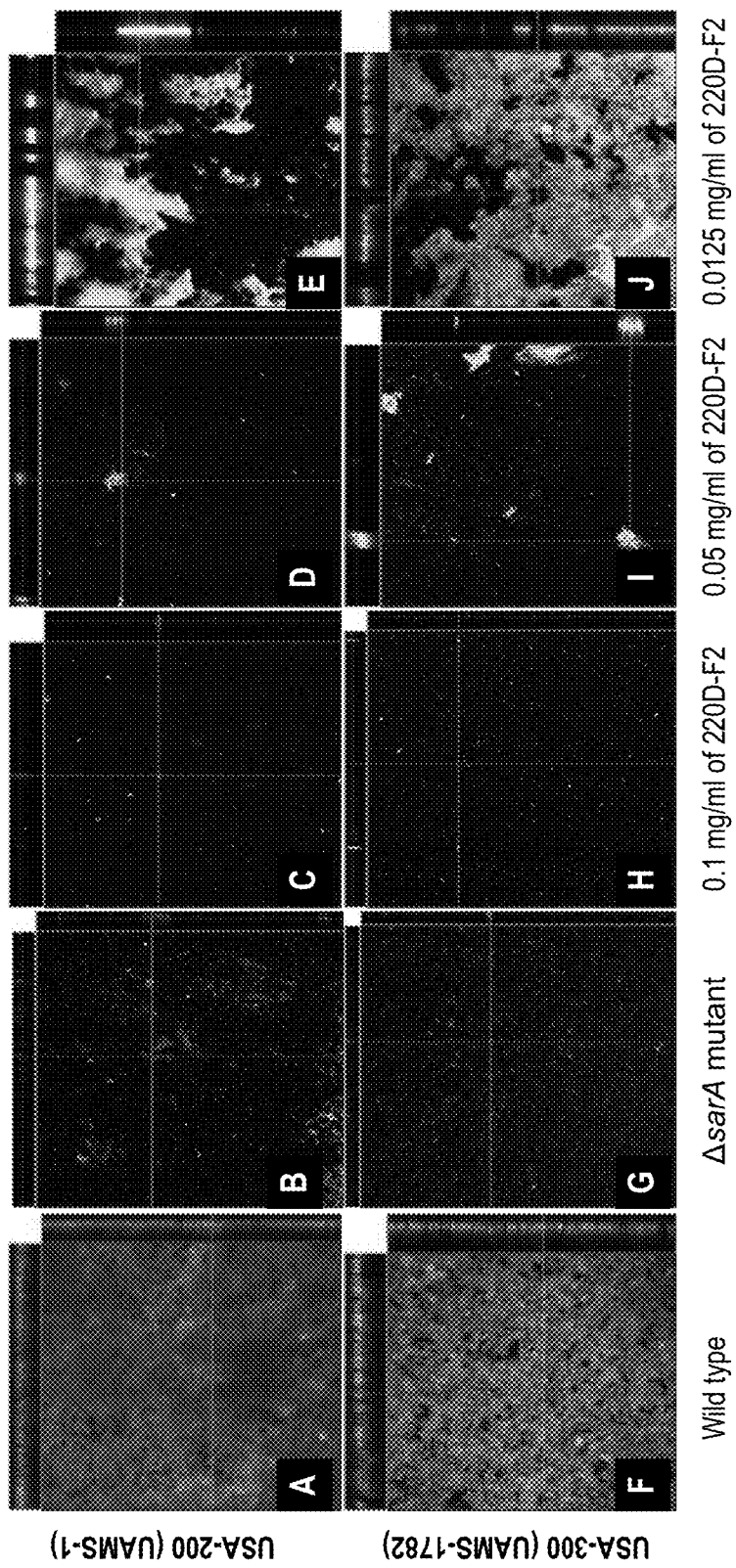
FIG. 6 presents confocal images of static biofilms. Images were collected after 20 h incubation. In order to assess the prophylactic capacity of the agent in inhibiting biofilm formation, wells were pre-treated with either 220D-F2 or the excipient alone (DMSO) at 0 h post-inoculation. An orthogonal view of the biofilms is used to depict the overall biofilm architecture at a magnification of 10×. (A-E) depict biofilms formed by UAMS-1 (USA200) and (F-J) are of UAMS-1782 (USA300) under the indicated test conditions.

The activity of 220D-F2 was assessed against each of 15 genotypically-diverse clinical isolates of *S. aureus*. TABLE 1 presents the results.

the USA300 isolate UAMS-1782 (FIG. 6). More specifically, the untreated wild-type strains formed relatively uniform biofilms ranging from 88-92 µm thickness while the isogenic sarA mutants formed very patchy biofilms with few isolated clumps of adherent cells. The wild-type strains treated with 220D-F2, like the untreated sarA controls, also formed very patchy biofilms as assessed by confocal microscopy at concentrations as low as 0.05 mg/ml.

Figure 7:
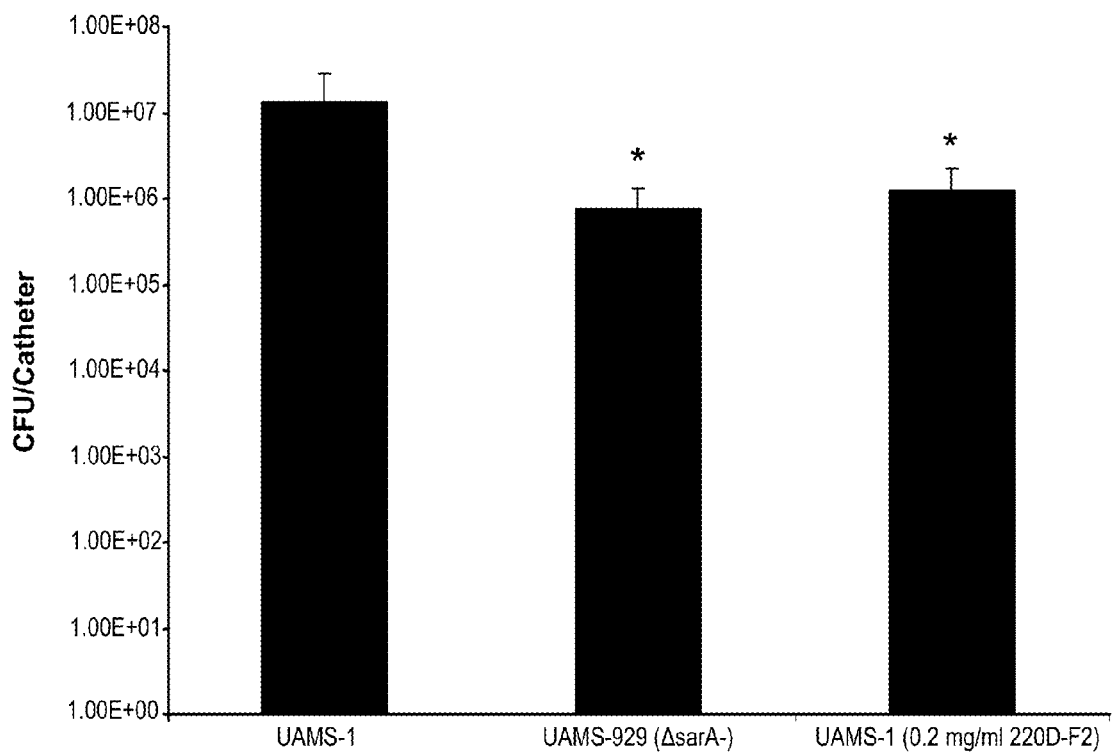
FIG. 7 illustrates the effect of fraction 220D-F2 on *S. aureus* biofilm formation in an in vitro catheter model. Bacteria treated with 220D-F2 (0.2 mg/ml) at the time of inoculation formed a significantly weaker biofilm ($P<0.05$) than the untreated control. Moreover, the level of biofilm formation was similar to that of the sarA mutant.

The inhibition of biofilm formation in the catheter assay was assessed by comparing the number of bacteria recovered from catheters colonized with UAMS-1 in the presence or absence of 220D-F2. It was that the total number of viable cells adherent to catheters following treatment with 220D-F2 during colonization was significantly reduced by comparison to the untreated control ($P<0.05$) and comparable to the number observed with the isogenic sarA mutant (FIG. 7). Although the actual reduction in the number of adherent cells was modest ($1.23 \times 10^6$ CFU/catheter in the presence of 220D-F2 versus $1.34 \times 10^7$ CFU/catheter in the untreated control), previous work comparing UAMS-1 with its isogenic sarA mutant demonstrated that a similar level of inhibition was sufficient to improve the therapeutic response of a biofilm-associated infection to antimicrobial therapy under both in

TABLE 1

Activity of 220D-F2 (mg/ml) against wild-type strains of *Staphylococcus aureus*.

| USA Type | Strain I.D. of wild type | Strain I.D. of sarA mutant | $MIC_{50}$ | $MIC_{90}$ | $MBC_{50}$ | $MBC_{90}$ | $MBIC_{50}$ | $MBIC_{90}$ |
|---|---|---|---|---|---|---|---|---|
| 100 | UAMS-1893 | UAMS-1941 | 0.38 | 0.53 | 0.53 | 0.74 | 0.1 | 0.2 |
| 200 | UAMS-1 | UAMS-929 | 0.38 | 0.53 | 0.74 | 1.04 | 0.05 | 0.05 |
|  | UAMS-270 | — | 0.38 | 0.53 | 1.46 | 2.04 | 0.1 | 0.2 |
|  | UAMS-601 | UAMS-950 | 0.53 | 0.74 | 1.46 | 2.04 | 0.05 | 0.1 |
|  | UAMS-1894 | UAMS-1945 | 0.38 | 0.53 | 0.74 | 1.04 | 0.05 | 0.1 |
| 300 | UAMS-1625 | UAMS-1653 | 0.38 | 0.53 | 0.53 | 0.74 | 0.05 | 0.1 |
|  | UAMS-1782 | UAMS-1804 | 0.38 | 0.53 | 0.38 | 0.53 | 0.05 | 0.1 |
|  | UAMS-1790 | UAMS-1796 | 0.38 | 0.53 | 0.38 | 0.53 | 0.05 | 0.1 |
| 400 | UAMS-1039 | UAMS-1938 | 0.53 | 0.74 | 0.53 | 0.74 | 0.1 | 0.2 |
| 500 | UAMS-1895 | UAMS-1942 | 0.74 | 1.04 | 1.04 | 1.46 | 0.1 | 0.2 |
| 600 | UAMS-1896 | UAMS-1943 | 0.53 | 0.74 | 0.53 | 1.04 | 0.1 | 0.2 |
| 700 | UAMS-1897 | — | 0.53 | 0.74 | 0.53 | 1.04 | 0.1 | 0.2 |
| 800 | UAMS-1898 | UAMS-1944 | 0.53 | 0.74 | 1.46 | 2.04 | 0.1 | 0.2 |
| 1000 | UAMS-1899 | UAMS-1930 | 0.53 | 0.74 | 1.04 | 1.46 | 0.1 | 0.3 |
| 1100 | UAMS-1900 | UAMS-1931 | 0.38 | 0.53 | 0.74 | 1.46 | 0.05 | 0.1 |

Figure 4:
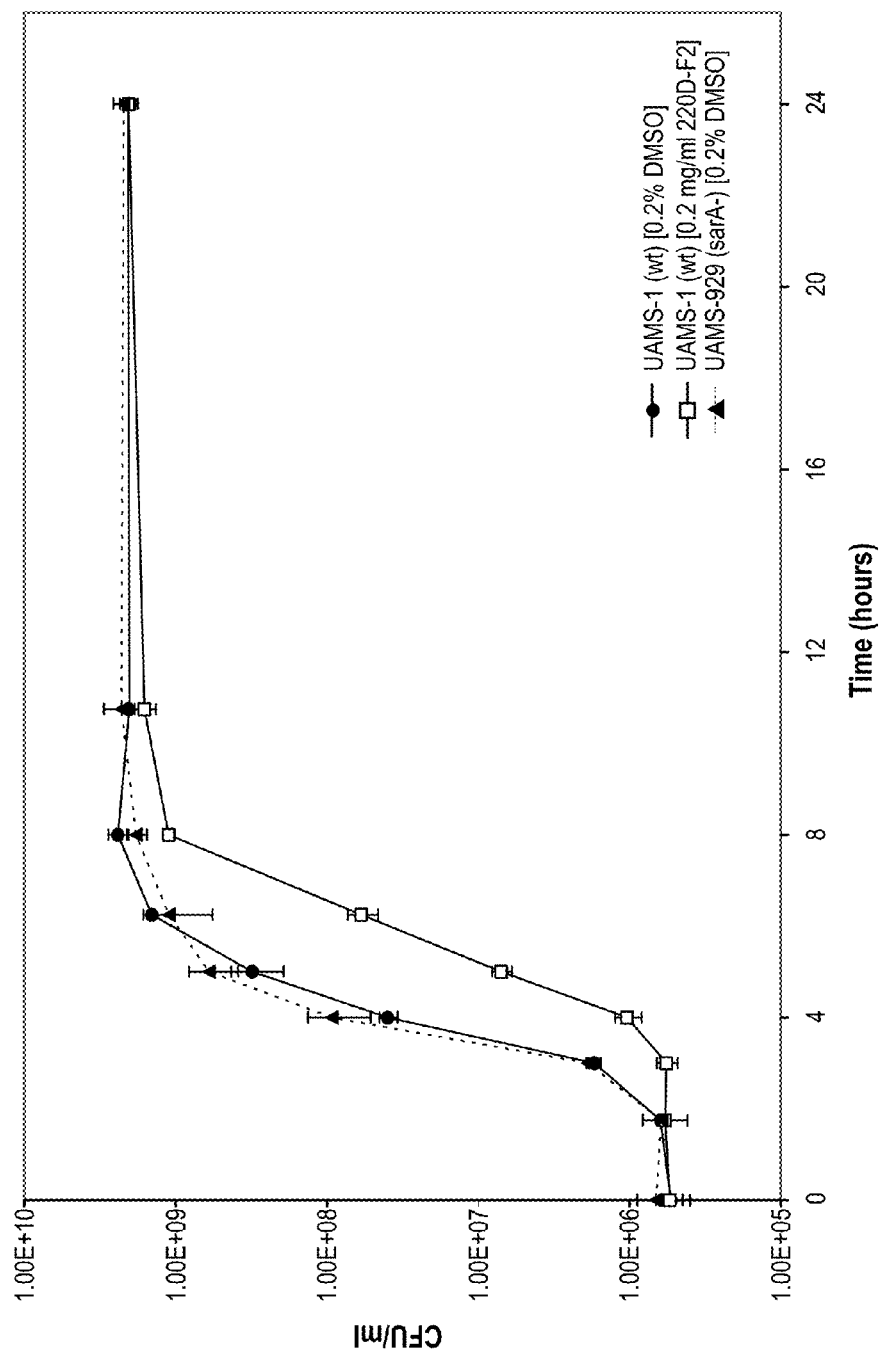
FIG. 4 illustrates the impact of fraction 220D-F2 on *S. aureus* growth. Plotted are growth curves of WT, WT+0.2 mg/mL 220D-F2, and sarA mutant cells.

The $MIC_{90}$ for all 15 strains ranged from 0.53-1.04 mg/ml, the $MBC_{90}$ ranged from 0.53-2.04 mg/ml, and the $MBIC_{90}$ ranged from 0.05-0.3 mg/ml. Thus, the $MBIC_{90}$ defined for each strain was in all cases at least 2-fold less than the $MIC_{90}$ and at least 4-fold less than the $MBC_{90}$. Furthermore, a growth curve established based on viable count over 24 hrs confirmed that, while the active fraction delayed entry into the exponential growth phase by ~2 hours, cultures with and without 220D-F2 reached the same density within 12 hrs and maintained the same cell counts throughout the stationary growth phase (FIG. 4). These findings suggest that 220D-F2 inhibits biofilm formation in a manner that is independent of its bacteriostatic or bactericidal activity.

Figure 5:
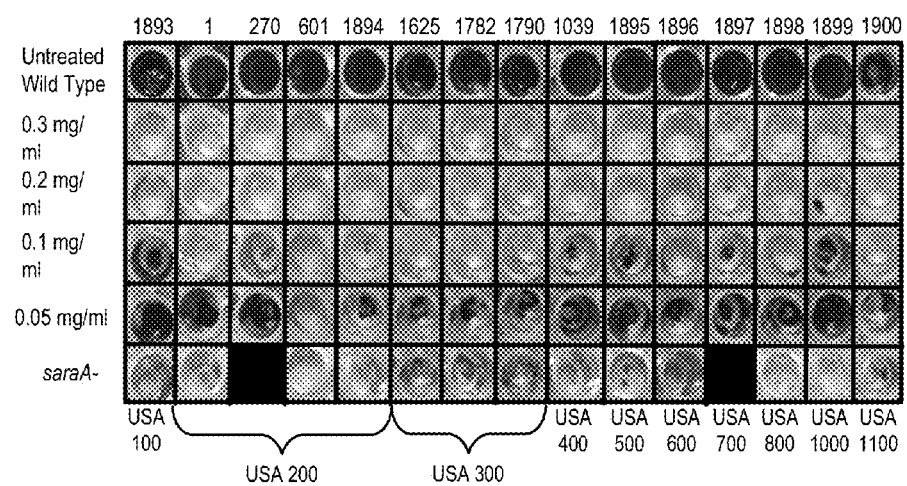
FIG. 5 shows the anti-biofilm activity of fraction 220D-F2. (A) Presented are microtiter plate in which the cells are stained with crystal violet, which assesses static biofilms. WT strains are identified according to their UAMS I.D. at the top of the image. The corresponding USA pulsed field type assignments are indicated at the bottom. The concentration of 220D-F2 added to the wells prior to inoculation is indicated on the left. The untreated wild type and its respective isogenic sarA mutant are also indicated here. (B) Cell density is plotted as a function of cells and/or treatment. A dose-response relationship between some of the plant fractions and bacteria was evident and all strains exhibited levels of biofilm inhibition approximating those of the corresponding isogenic sarA mutant controls. The statistical significance of the difference between the untreated and treated wells is denoted with * ($P<0.05$) and ∀ ($P<0.001$). All of the corresponding isogenic sarA mutants were significantly different from the wild type at $P<0.001$.
Figure 5:
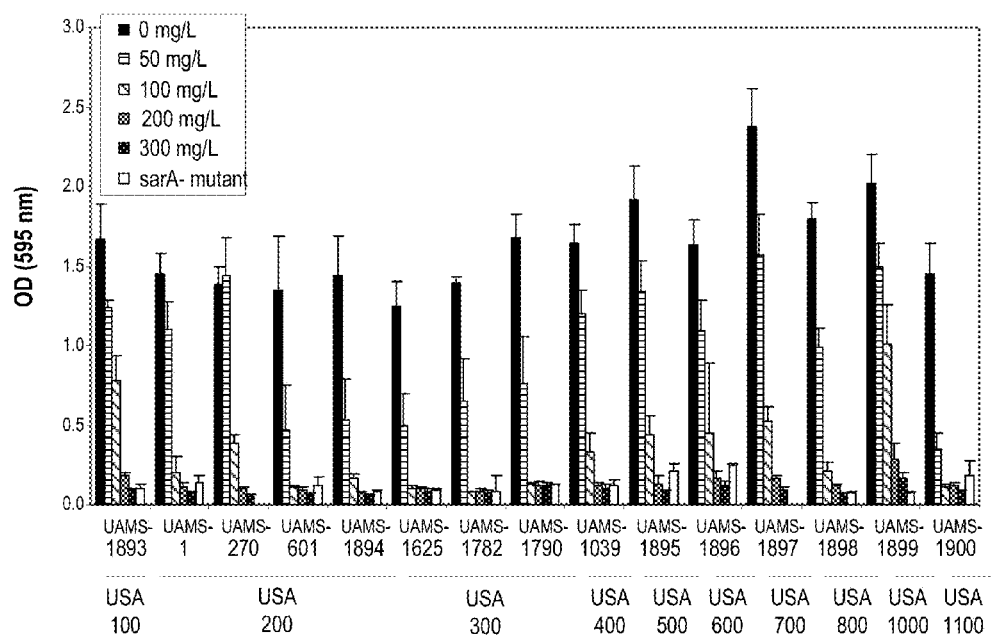

The addition of 220D-F2 inhibited biofilm formation in a concentration-dependent manner in all 15 *S. aureus* isolates examined (see FIG. 5). The degree of inhibition was comparable to that observed with the isogenic sarA mutants at concentrations as low as 0.1 mg/ml and, in some cases, 0.05 mg/ml. This was confirmed by confocal microscopy demonstrating that 220D-F2 inhibited biofilm formation to a degree comparable to isogenic sarA mutants in both UAMS-1 and vitro and in vivo conditions (Weis et al., 2009a, Antimicrobial Agents and Chemotherapy 53:4096-4102).

Example 3

Activity of Phenolic-Rich Fraction Against Established Biofilm

The following example details the inability of the active fraction 220D-F2 to disrupt an established biofilm, but details the synergistic activity of the active fraction and an antibiotic to limit the growth of cell embedded in an established biofilm. In vitro catheter assays were used to assess biofilm cell viability.

In Vitro Catheter Assays.

UAMS-1 was grown on 1 cm catheter segments as previously described (Weiss et al., 2009b, Antimicrobial Agents and Chemotherapy 53:2475-2482). After 24 hrs, the BM medium was replaced with BM medium containing 220D-F2 (0.2 mg/ml) and/or daptomycin. The concentration of daptomycin used in these experiments was 10-fold higher (10 µg/ml) than the breakpoint MIC (1.0 µg/ml) defined for a daptomycin-sensitive strain of *S. aureus* by the Clinical and Laboratory Standards Institute (CLSI). The medium was replaced in its entirety at 24 hr intervals for 7 days. The therapeutic response of UAMS-1 to daptomycin in the presence of 220D-F2 was assessed by comparison to UAMS-929 grown in the absence of 220D-F2 but exposed to daptomycin as previously described (Weiss et al., 2009a, 2009b, supra). Specifically, the treatment groups employed for these experiments were 1) UAMS-1 with 0.2% DMSO as a excipient control, 2) UAMS-1 with 0.2 mg/ml 220D-F2 in DMSO, 3) UAMS-1 with 0.01 mg/ml daptomycin, 4) UAMS-1 with 0.2 mg/ml 220D-F2 and 0.01 mg/ml daptomycin, 5) UAMS-929 with the 0.2% DMSO excipient control and 6) UAMS-929 with 0.01 mg/ml daptomycin. After each 24 h interval, catheters were removed from each treatment group and rinsed with PBS before removing bacteria for plate counts as previously described (Weiss et al., 2009a, 2009b, supra).

This assay was also used to assess the prophylactic activity of 220D-F2. In this case, the test compounds were added to the BM at the time of inoculation rather than after a 24 hr colonization period. After 24 hr incubation in the presence of 220D-F2, the catheters were processed for plate counts as described above. To assess the response to adjunct therapy following prophylaxis (220D-F2 present during colonization), a final experiment was conducted in which catheters were exposed to 220D-F2 during colonization and then exposed to the same treatment groups described above starting 24 hours after inoculation.

Results.

Figure 8:
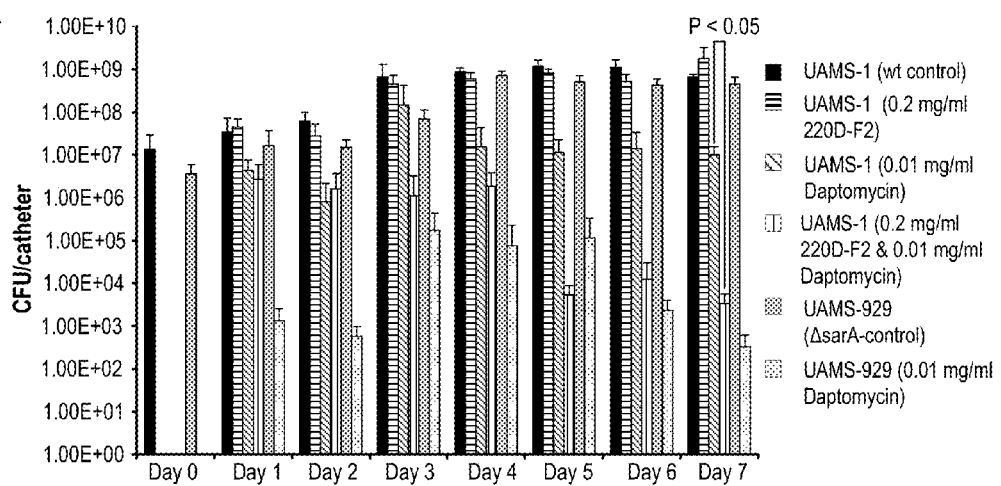
FIG. 8 shows the ability of fraction 220D-F2 alone or in combination with daptomycin to disrupt established biofilms using a catheter model. (A) Catheters were colonized in the absence of any extract. A trend is apparent that shows the reduction of biofilm in catheters treated with both 220D-F2 (0.2 mg/mL) and daptomycin (0.01 ml/mL). The difference between catheters treated with daptomycin and 220D-F2 as compared to those treated with daptomycin alone is significant ($P<0.05$) on day 7. (B) Catheters were colonized in the presence of 0.2 mg/ml 220D-F2, resulting in the formation of a weakened biofilm on Day 0, roughly equivalent to that of the sarA mutant. An improved efficacy of treatment with both 220D-F2 and daptomycin (compared with daptomycin alone) is apparent as early as Day 1 ($P<0.05$).
Figure 8:
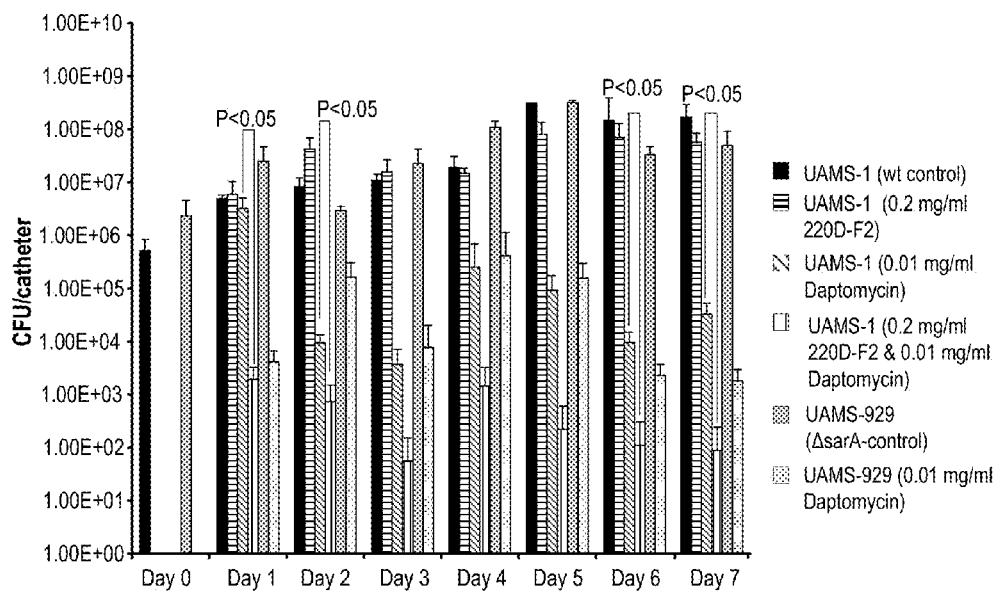

These results demonstrate that when 220D-F2 was added to a previously established (24 h) biofilm, no disruption occurred even after 7 consecutive days of exposure (FIG. 8A). Thus, while 220D-F2 was effective at initially interrupting attachment and biofilm formation (see Example 2), it was ineffective at disrupting an established biofilm. However, given its relative lack of bacteriostatic or bactericidal properties, the possibility of synergism between 220D-F2 and conventional antibiotics in disrupting an established biofilm was explored.

For this, tests were conducted using 0.2 mg/ml 220D-F2 together with daptomycin at a concentration of 10× the breakpoint MIC defined for a daptomycin-sensitive strain of *S. aureus* (1.0 μg/ml). These tests revealed that the combination of 220D-F2 and daptomycin was more effective than either agent alone (FIG. 8A). This difference was most apparent at day 7, with catheters exposed to both 220D-F2 and daptomycin exhibited average colony counts of $3.37 \times 10^3$ CFU/catheter and those exposed to daptomycin alone exhibited colony counts of $1.01 \times 10^7$. However, despite this almost 5-log reduction, none of these catheters exposed to both 220D-F2 and daptomycin were cleared of all viable cells. When catheters were colonized in the presence of 220D-F2, a weakened biofilm was formed. Exposure to both 220D-F2 and daptomycin resulted in decreased cell numbers by day 1 (FIG. 8B). Moreover, one out of three catheters were cleared of all adherent cells when treated with both 220D-F2 and daptomycin on days 2 and 4, and two out of three catheters were cleared on days 3, 5, 6, and 7.

Example 4

Combinations of Phenolic-Rich Fraction and Antibiotics Limit Growth of Established Biofilm The synergistic activity of the phenolic-rich faction and additional antibiotics was examined in more detail. A catheter model for the disruption of an established biofilm (essentially as detailed in Example 3) was used to assess the therapeutic capacity of 220D-F2 in eliminating an established biofilm as an adjunct therapy to antibiotics at 1× and 10× the CLSI-established MIC breakpoint.

Catheters were colonized with UAMS-1 in the absence of any extract. After 24 hours, the catheters were exposed to 220D-F2 (200 mg/L); antibiotic at 1× the breakpoint MIC; antibiotic at 1× the breakpoint MIC+200 mg/L 220D-F2; antibiotic at 10× the breakpoint MIC; antibiotic at 10× the breakpoint MIC+200 mg/L 220D-F2. The antibiotics tested were daptomycin, clindamycin, vancomycin, and oxacillin.

These experiments revealed that there was a reduction of biofilm in catheters treated with both 220D-F2 and antibiotic in all cases examined. The results confirm those presented above in Example 3 that the phenolic-rich faction alone does not affect growth of an established biofilm. FIG. 9A presents cell growth in the catheter biofilm in the presence of 220D-F2, daptomycin, and combinations thereof. The difference between catheters treated with daptomycin at 1× the MIC (1 mg/L) and 220D-F2 as compared to those treated with daptomycin alone was significant at P<0.001 on days 3 and 6 and at P<0.05 on day 7. The difference between those treated with 10× the MIC (10 mg/L) alone versus the adjunct therapy with 220D-F2 is significant (P<0.05) on day 7.

Biofilm growth in the presence of combinations of 220D-F2 and clindamycin is presented in FIG. 9B. The difference between catheters treated with clindamycin at 1× the MIC (0.5 mg/L) and 220D-F2 as compared to those treated with clindamycin alone was significant at P<0.05 on days 2, 5, and 7 and at P<0.001 on day 6. The difference between those treated with 10× the MIC (5 mg/L) alone versus the adjunct therapy with 220D-F2 was significant at P<0.001 on days 5 and 7 and at P<0.05 on day 6. Thus, there was a ~2.5 log reduction in biofilm on treatment days 4-7 for the catheters treated with 220D-F2 and 5 mg/L clindamycin (10× the breakpoint MIC) in comparison to clindamycin therapy alone. Although evident to a lesser extent (0.5-1 log reduction) in the treatment groups receiving 0.5 mg/L clindamycin (1× breakpoint MIC), the group receiving the adjunct therapy (extract plus antibiotic) did demonstrate a significant treatment advantage over clindamycin therapy alone on days 2, 5, 6, and 7.

FIG. 9C presents growth of cells in the biofilm in the presence of 220D-F2, vancomycin, and combinations thereof. The difference between catheters treated with vancomycin at 1× the MIC (2 mg/L) and 220D-F2 as compared to those treated with vancomycin alone was significant (P<0.05) on days 3, 4 and 6. The difference between those treated with 10× the MIC (20 mg/L) alone versus the adjunct therapy with 220D-F2 was significant (P<0.05) on days 3 and 7. Thus, a small advantage (0.5-1 log reduction) was evident in the adjunct therapy groups (220D-F2 plus vancomycin) over vancomycin alone for both the 1× and 10× (2 and 20 mg/L) test concentrations. This advantage was significant for the 1× test groups on days 3, 4, and 6 and significant for the 10× test groups on days 3 and 7.

Biofilm growth in the presence of 220D-F2, oxacillin, and combinations thereof is presented in FIG. 9D. The difference between catheters treated with oxacillin at 1× the MIC (0.5 mg/L) and 220D-F2 as compared to those treated with oxacillin alone was significant at P<0.001 on days 1, 2, 4 and 6 and at P<0.05 on days 3, 5 and 7. The difference between those treated with 10× the MIC (5 mg/L) alone versus the adjunct therapy with 220D-F2 was significant (P<0.05) on day 7. Thus, catheters treated with an adjunct therapy of oxacillin plus 220D-F2 demonstrated a 0.5-2 log advantage over those treated with oxacillin alone in the 10× (5 mg/L) treatment groups and a 2-5 log reduction (increasing with the number of treatment days) for the 1× (0.5 mg/L) treatment groups. This advantage was statistically significant for all treatment days in the 1× treatment groups and on day 7 for the 10× groups. Moreover, 25% of catheters treated with 10× oxacillin plus 220D-F2 were cleared of all adherent cells by day 6 of treatment and 50% were cleared by day 7.

Example 5

Fractionation of Active Fraction and Activity of Additional Fractions

A preparative reversed-phase high-performance liquid chromatography (RP-HPLC) method was developed to further separate 220D-F2 into four fractions. Briefly, 220D-F2 was dissolved in 2-propanol:water (2:8) at a concentration of 50 mg/mL. A C-18 column (μBondapak™, 19 mm×300 mm, 125 Å, 10 μm) was used to separate 1 mL injections (total 5 mg) with a Waters 600E system controller and pump and an isocratic mobile phase of $H_2O$:acetonitrile:2-propanol:formic acid (74:17:8:1) at a flow rate of 7 mL/min (all solvents HPLC-grade, Fisher Chemical) and detection at a wavelength of 360 nm using a Waters 486 Tunable Absorbance Detector and Shimadzu C-R5A Chromatopac. Fractions were collected at 17.5 (220D-F2-f1), 20.5 (-f2), 27 (-f3) and 45 (-f4) minutes. The largest single peaks were located in fractions 2 and 3, whereas fractions 1 and 4 contained multiple minor peaks. The fractions were assayed for inhibition of biofilm formation essentially as described in Example 1. The minimum biofilm-inhibiting concentration (MBIC) was defined as the lowest concentration of extract in which biofilm formation was limited to a level ≥90% (for $MBIC_{90}$) or ≥50% (for $MBIC_{50}$) by comparison to the untreated parent control strain.

Figure 10:
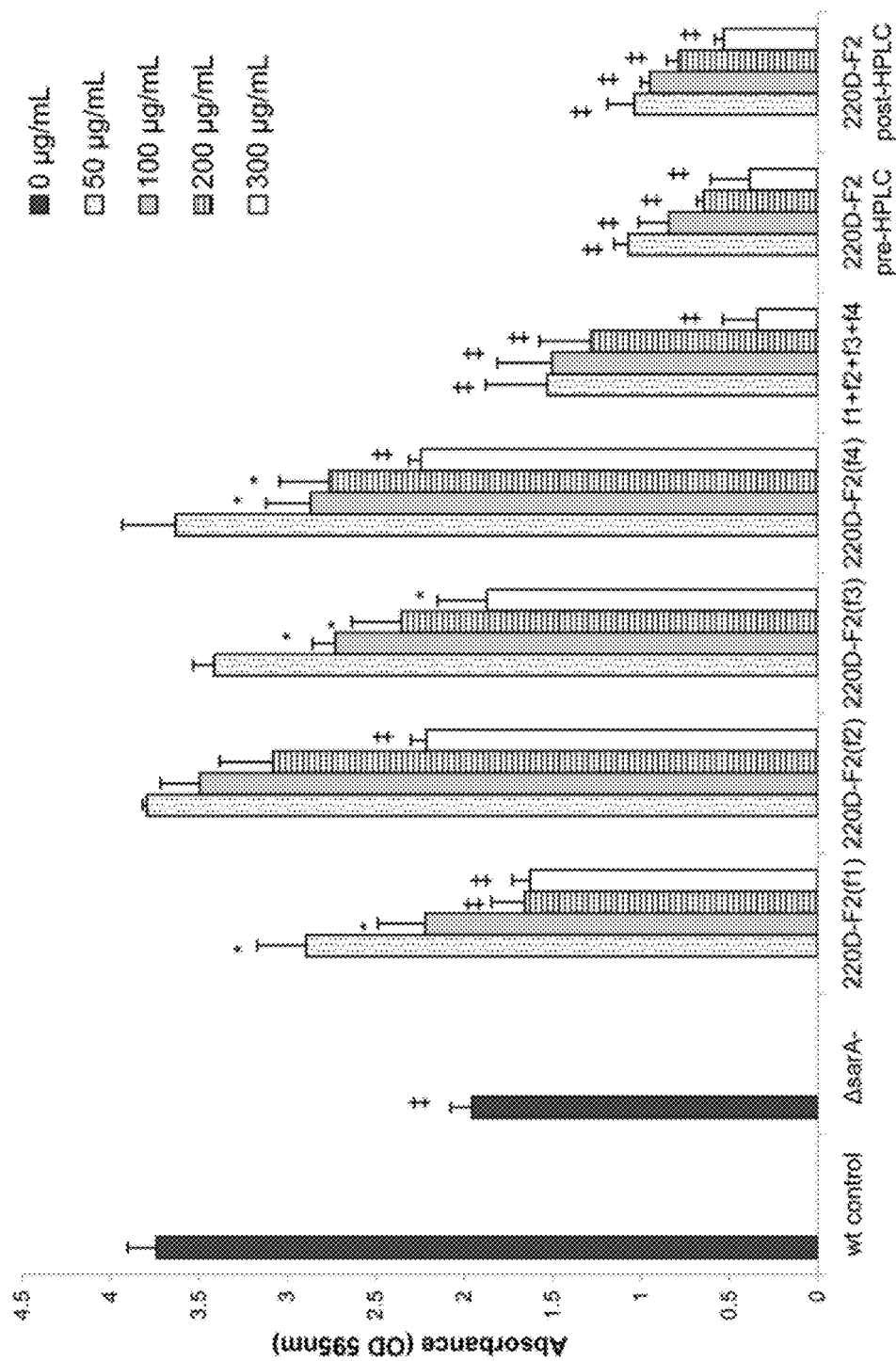
FIG. 10 presents inhibition of biofilm formation by fractions of 220D-F2. A static microtiter plate biofilm assay was used to assess the inhibitory activity of fractions of 220D-F2 both alone and in combination using UAMS-1. No single fraction of 220D-F2 exhibited improved biofilm-inhibiting activity over 220D-F2 as a whole. Multiple combinations of the fractions were made and the only combination which resulted in restoration of activity on the same level as 220D-F2 was when all 4 fractions (f1+f2+f3+f4) were recombined. Likewise, a single collection, in which 220D-F2 was run through the HPLC system and collected as a whole (instead of splitting into fractions) also resulted in the same level of activity as the original 220D-F2. Statistical significance (*, $P<0.05$; ∀, $P<0.001$) refers to differences observed in comparison to the untreated control.
Figure 11A:
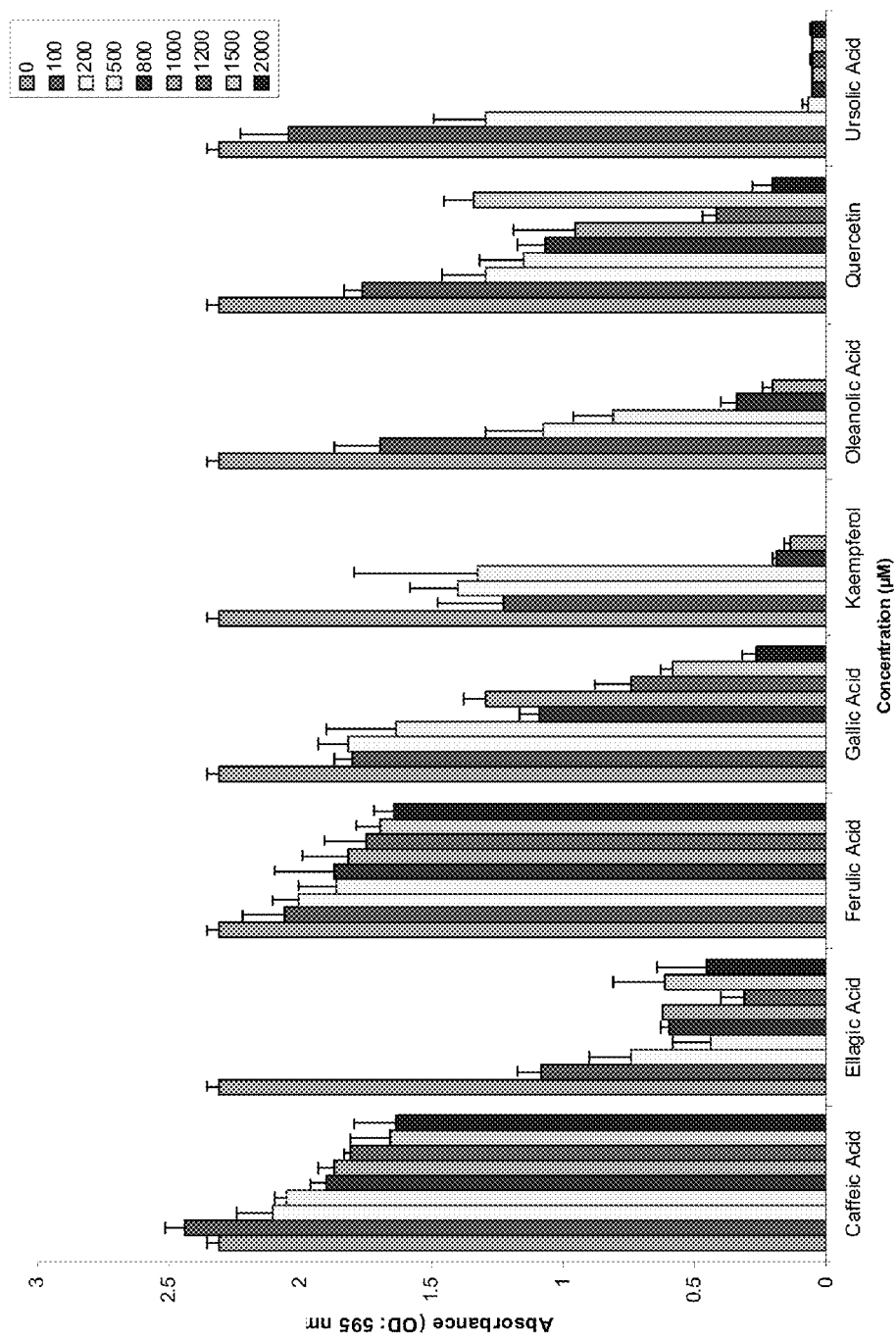
FIG. 11A shows the inhibition of biofilm formation by the indicated compounds against UAMS-1, a clinical osteomyelitis methicillin-sensitive strain of *S. aureus* using a static microtiter biofilm assay.
Figure 11B:
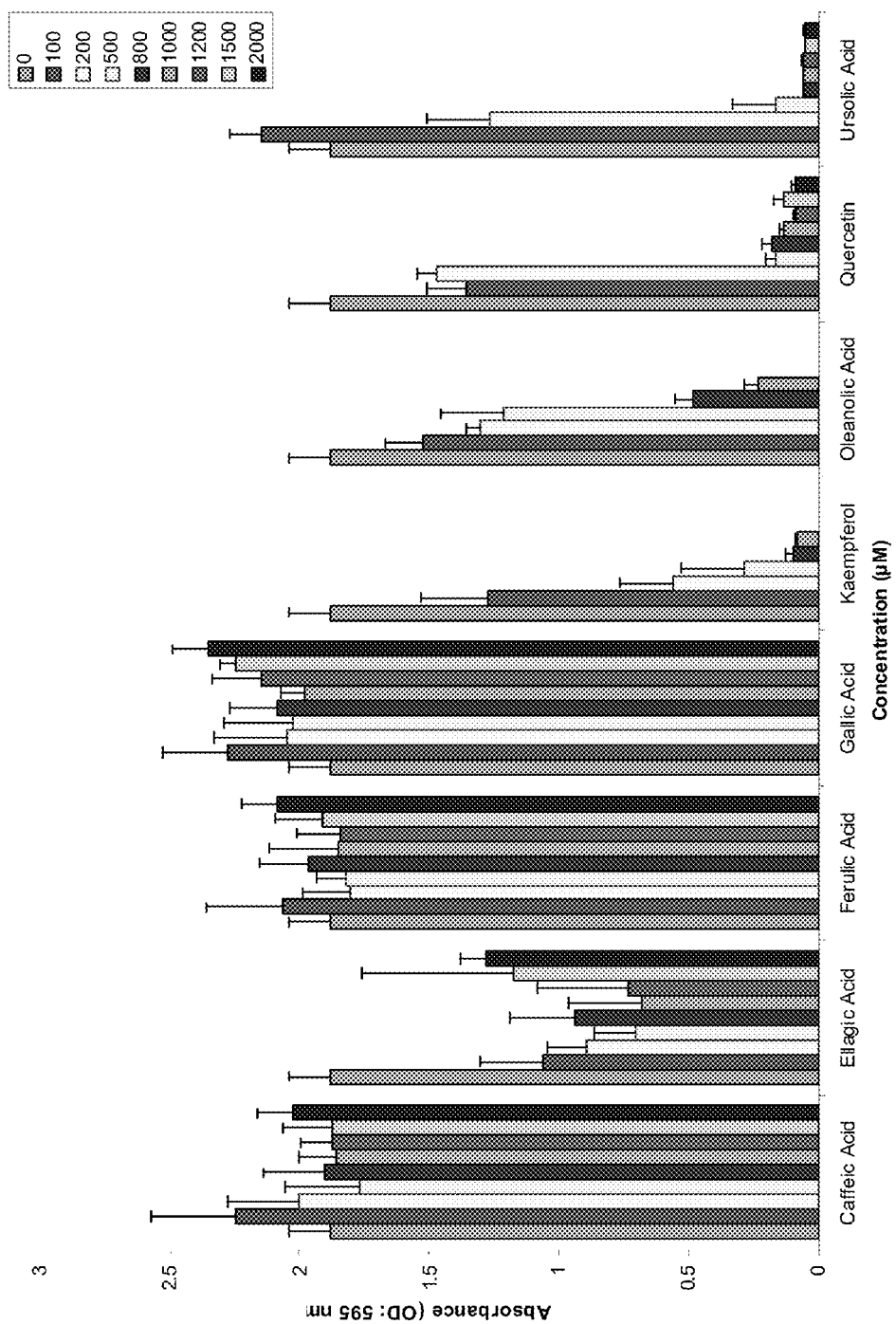
FIG. 11B shows the inhibition of biofilm formation by the indicated compounds against UAMS-1625, a clinical brain abscess *S. aureus*, methicillin resistant strain, using a static microtiter biofilm assay.
Figure 11C:
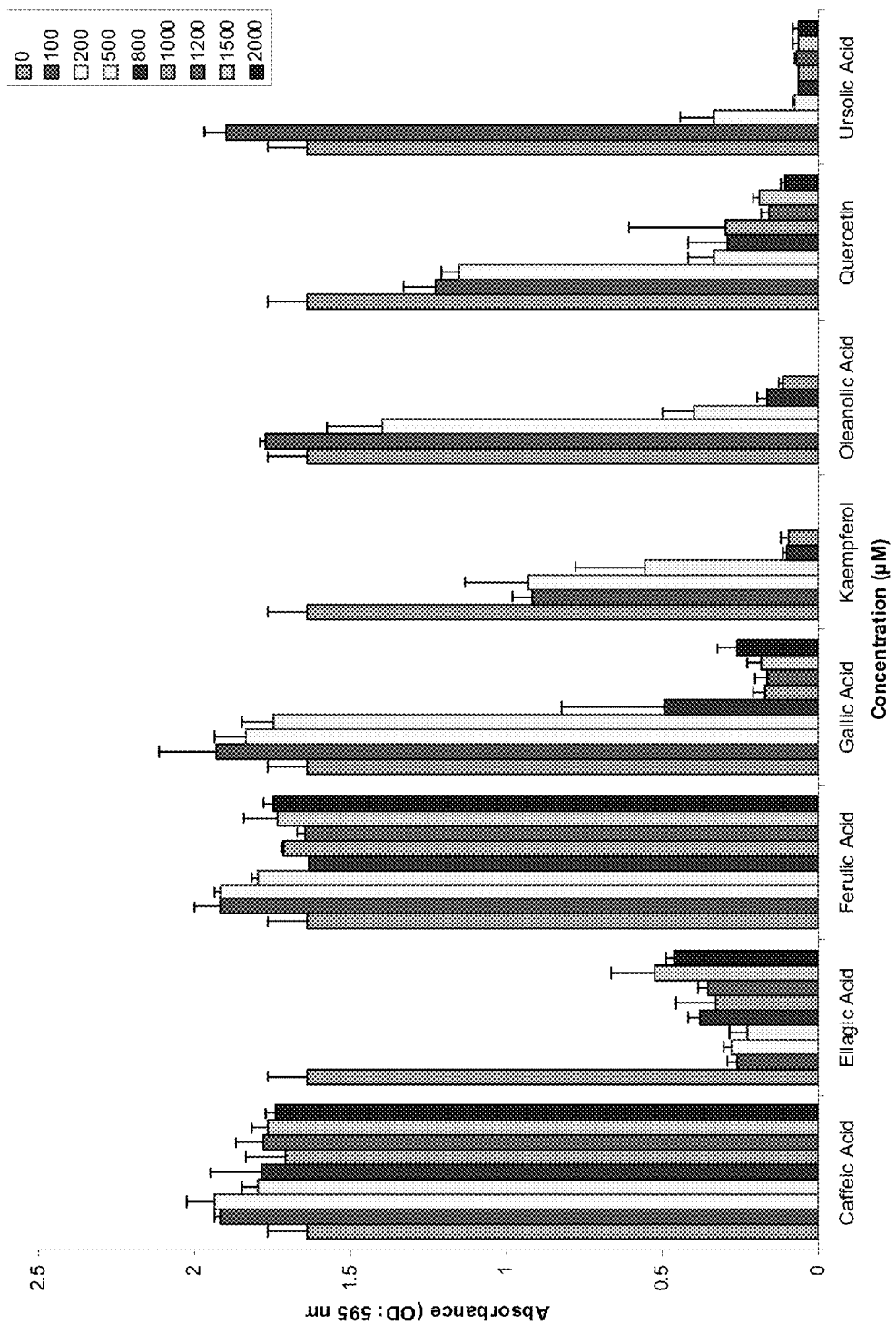
FIG. 11C shows the inhibition of biofilm formation by the indicated compounds against UAMS-1864, a clinical bloodstream *S. aureus*, methicillin-resistant strain, using a static microtiter biofilm assay.
Figure 11D:
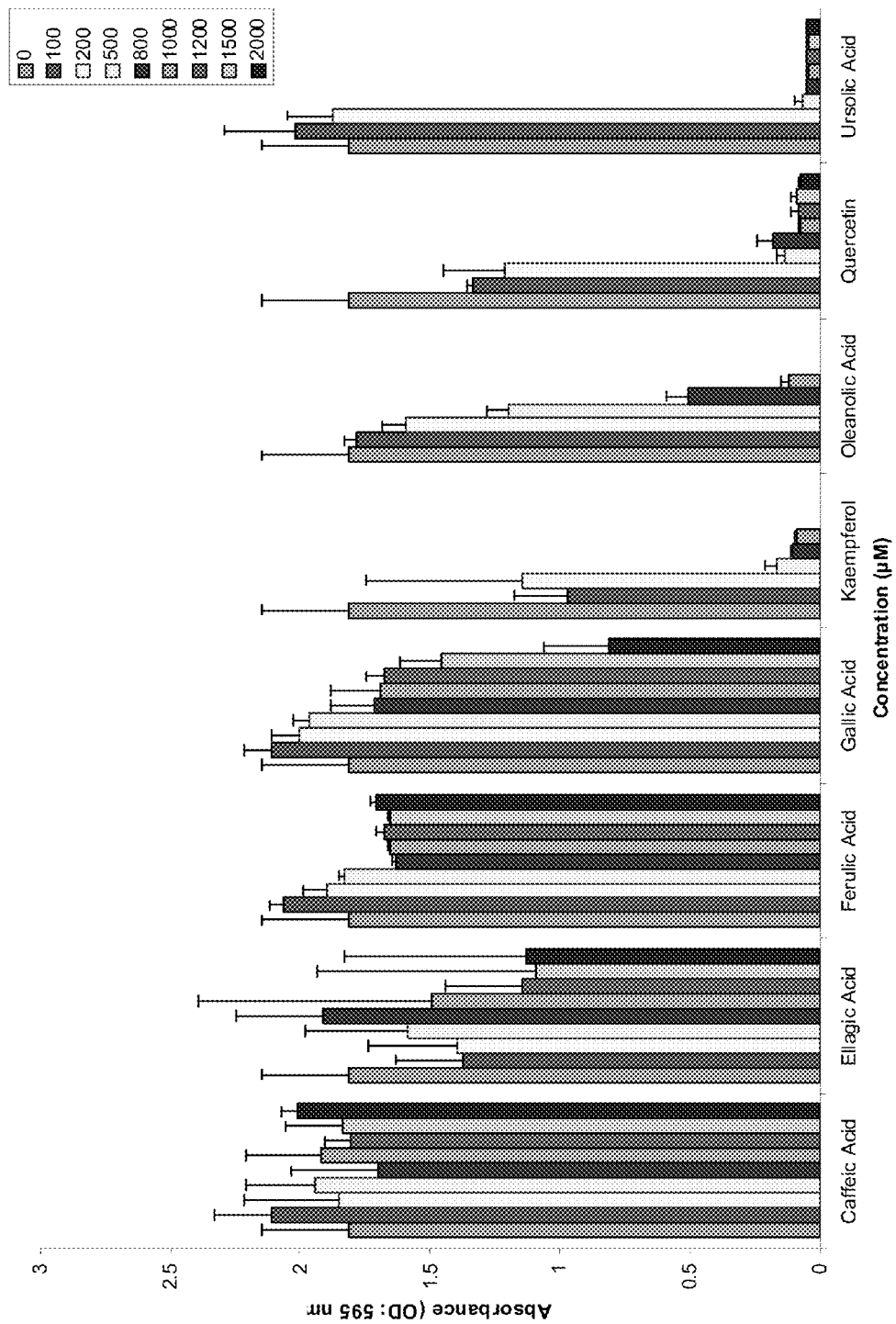
FIG. 11D shows the inhibition of biofilm formation by the indicated compounds against UAMS-1865, a clinical bloodstream *S. aureus* isolate, methicillin resistant strain, using a static microtiter biofilm assay.
Figure 11E:
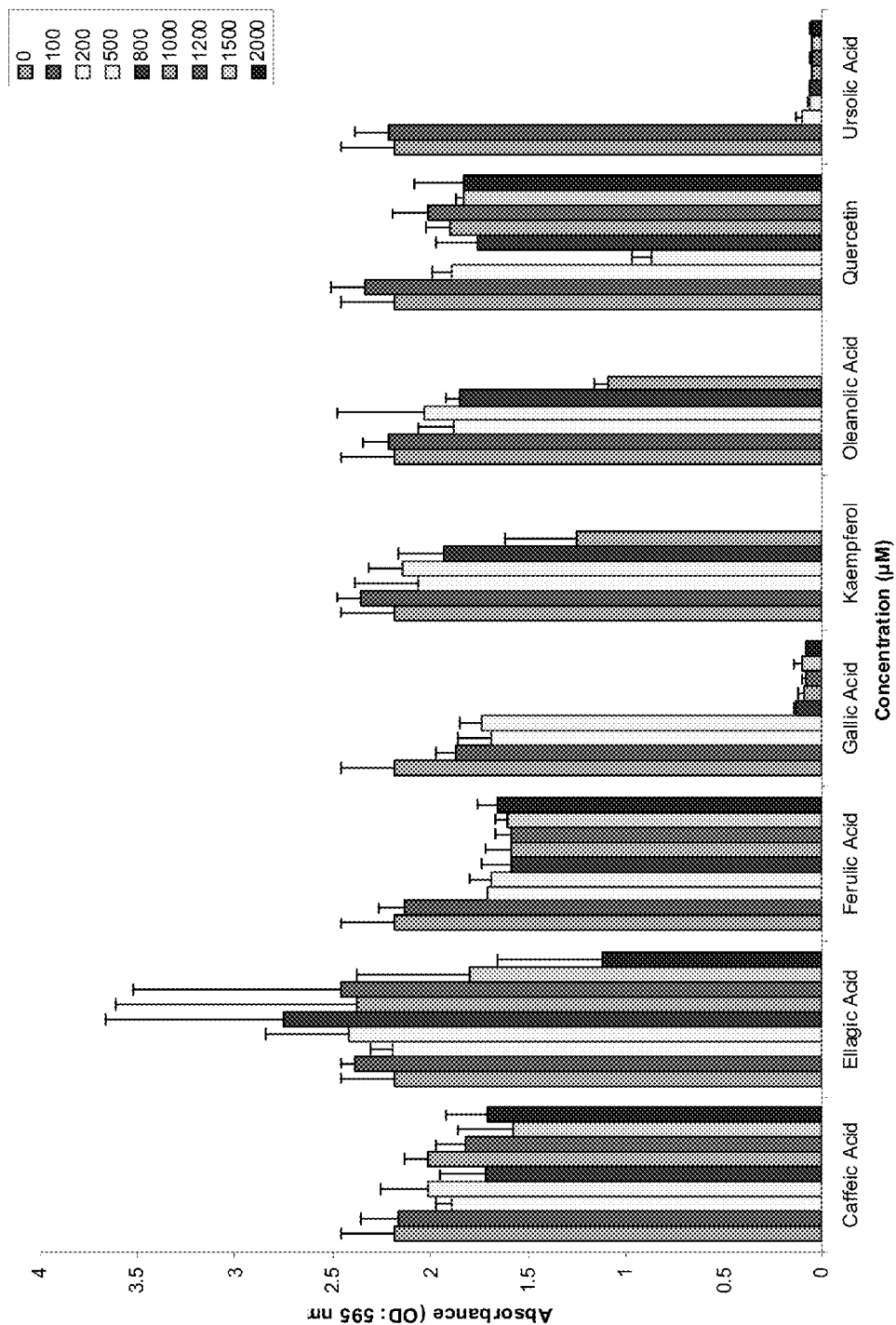
FIG. 11E shows the inhibition of biofilm formation by the indicated compounds results against UAMS-302, a methicillin sensitive isolate of *S. epidermidis*, using a static microtiter biofilm assay.
Figure 11F:
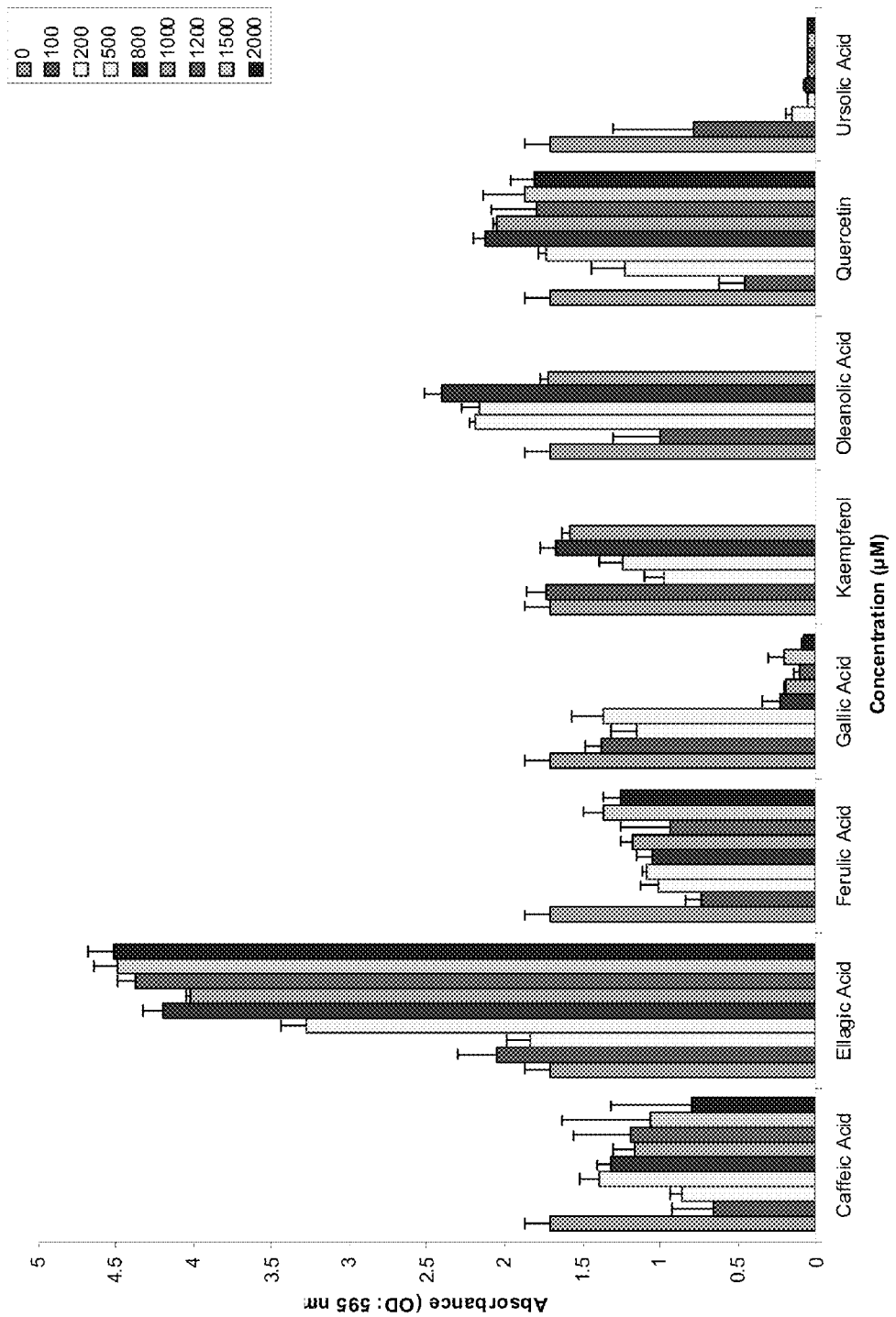
FIG. 11F shows the inhibition of biofilm formation by the indicated compounds against UAMS-1037, a clinical catheter sepsis *S. epidermidis* isolate, methicillin resistant strain, using a static microtiter biofilm assay.

Bioassays for biofilm inhibition with these fractions revealed that no single fraction was more effective than 220D-F2 as a whole, suggesting that more than one fraction was necessary for the anti-biofilm activity (FIG. 10). Thus, additional experiments were conducted in which fractions were combined in all possible permutations and tested for activity (data not shown). The only combination in which activity was restored was when all four fractions were recombined (FIG. 10). These results were also compared with 220D-F2 before and after running through the HPLC system to determine if the separation protocol itself had any effect on the activity. No significant difference between samples could be determined. These data suggest that the anti-biofilm effect of 220D-F2 is due to the synergistic activity of multiple compounds, and the relative proportions of this mixture is important to the activity.

Example 6

Liquid Chromatography Tandem Mass Spectrometry Analysis of Active Fraction

Further characterization of 220D-F2 (suspended in 5% isopropanol in H2O, 1 mg/mL) was performed using accurate mass liquid chromatography-ultraviolet absorption-tandem mass spectrometry (LC/UV/MS/MS) to identify the major components. A Mac-Mod HALO C18 column (3.0×100 mm) was used with a mobile phase (A: 0.1% formic acid in water; B: 0.1% formic acid in acetonitrile) with a gradient (hold 2% B for 2 min., 2-50% B over 18 min, 100% B for 5 min.), flow of 0.4 mL/min and PDA (photodiode array detector) detection range of 200-790 nm. MS detection was with a Thermo LTQ Orbitrap Discovery, +ESI mode, and scan range of 140-2000 Da. Searches of multiple databases (Human Metabolome Database (version 2.5), ChemSpider, SciFinder, and Kyoto Encyclopedia of Genes and Genomes (KEGG) LIGAND Database) were performed using chemical formula queries. All mass measurements were within 0.5 mmu of the proposed formulae, well within the expected measurement tolerances of the mass spectrometer.

This analysis revealed the presence of ellagic acid (EA) and several ellagic acid derivatives (EADs) or sapogenin-related compounds. Molecular formulas of $C_{14}H_6O_8$, $C_{20}H_{16}O_{12}$, $C_{19}H_{14}O_{12}$, $C_{30}H_{46}O_7$, $C_{30}H_{46}O_8$ (Table 2) were identified and confirmed with accurate mass measurements (<5 ppm). Of the major UV components identified, the most abundant was ellagic acid (#2, MW 302). The second most abundant UV component (#7) did not yield a clear MS signal. The third most abundant UV component (#1, MW 434) appears to be ellagic acid plus a $C_5H_8O_4$ moiety. A fourth UV component (#3, MW 448) was found to be consistent with a glycosylated derivative of ellagic acid. Investigation of the possible formulae consistent with the mass measurement of the fifth UV component (#4) did not yield sufficient data for proposal of a structure. Of the major MS components, the most abundant (#8) did not yield enough information to support the proposal of a structure, however the molecular weights and mass defects suggest that they may be dimers of MW-500 species (similar to #6). The second most abundant MS component (#6) is consistent with a sapogenin. Successive loss of water (m/z 18) is consistent with a poly-hydroxylated compound. The third most abundant MS component (#5, MW 534) appears to be similar to #6 and has MS/MS losses consistent with a multiply hydroxylated compound like a sapogenin. Losses consisted with neutral loss of a sugar were not observed.

TABLE 2

Compounds Detected in Extract 220D-F2 by Accurate Mass LC/UV/MS/MS.

| # | Proposed Compound† | Molecular Formula | Retention Time (minutes) | $[M + H]^+$ m/z | MS-MS Fragmentation (m/z) |
|---|---|---|---|---|---|
| 1 | Ellagic acid xylopyranoside or Ellagic acid xylofuranoside | $C_{19}H_{14}O_{12}$ | 10.9 | 435.05594 | 303.01346 |
| 2 | Ellagic acid | $C_{14}H_6O_8$ | 11.1 | 303.01354 | 285.00281, 275.01868, 259.02338, 241.01314 |
| 3 | Ellagic acid mannopyranoside | $C_{20}H_{16}O_{12}$ | 11.1 | 449.07158 | 352.33952, 303.01366, 249.11220, 182.98514 |

TABLE 2-continued

Compounds Detected in Extract 220D-F2 by Accurate Mass LC/UV/MS/MS.

| # | Proposed Compound† | Molecular Formula | Retention Time (minutes) | [M + H]+ m/z | MS-MS Fragmentation (m/z) |
|---|---|---|---|---|---|
| 4 | unknown | unknown | 11.5 | 437.97815 | 409.09189, 303.01351, 219.10153, 182.98507 |
| 5 | Sapogenin derivative | $C_{30}H_{46}O_8$ | 13.5 | 535.32637 | 517.31604, 499.30499, 481.29480, 469.29486 |
| 6 | Sapogenin derivative | $C_{30}H_{46}O_7$ | 13.7 | 519.33139 and 501.32097 | 501.32071, 483.31012, 473.32559, 455.31543, 437.30457, 409.30994 |
| 7 | unknown | unknown | 14.7 | 573.98540 and 396.98622 | 532.95864, 505.35274, 485.32649, 451.99400, 440.95009, 352.33958, 317.02929, 273.07586, 199.98796, 182.98517 |
| 8 | unknown | unknown | 16.9 | 1017.62898 and 999.61893 | 955.62813, 937.61896, 499.30520, 437.30489 |

Possible structures for three of these compounds ($C_{14}H_6O_8$, $C_{20}H_{16}O_{12}$, $C_{19}H_{14}O_{12}$) are shown in Table 3.

TABLE 3

Structures of Compounds Identified in Extract 220D-F2

| Compound | Molecular Formula | Structure |
|---|---|---|
| 1 Ellagic acid xylopyranoside or Ellagic acid xylofuranoside | $C_{19}H_{14}O_{12}$ | 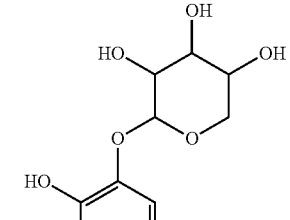 or 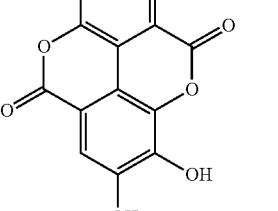 |
| 2 Ellagic acid | $C_{14}H_6O_8$ | 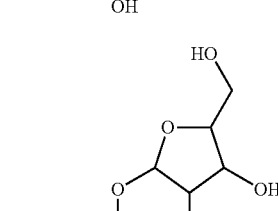 |
| 3 Ellagic acid mannopyranoside | $C_{20}H_{16}O_{12}$ | 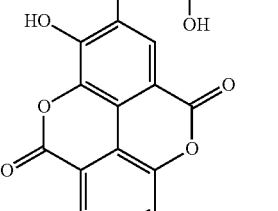 |

Example 7

Anti-Biofilm Activity of *R. ulmifolius* Phytochemicals

Ten commercially available phytochemical constituents reported in the literature to have been isolated from *R. ulmi-* folius (Table 4) were purchased and examined for their prophylactic efficacy in the prevention of biofilm formation using a static microtiter plate biofilm assay. Ferulic acid, kaempferol, ursolic acid, quercetin dehydrate, caffeic acid, ellagic acid, and oleanolic acid were purchased from MP BioMedicals (Solon, Ohio, USA); quercetin-3-O-glucuronide and tiliroside from Chromadex (Irvine, Calif., USA); and gallic acid from Acros Organics (NJ, USA). Compounds were tested for growth and biofilm inhibitory activity at doses ranging from 25-2000 μM. To determine the minimum inhibitory concentration (MIC) for each fraction, strains of S. aureus were grown in 37° C. in cation adjusted Muller-Hinton broth (CAMHB). MIC and MBC were determined following Clinical and Laboratory Standards Institute (CLBI) broth microdilution guidelines. Briefly, strains were inoculated into 0.1 ml CAMBH containing varying concentrations of the compound. For MIC, optical density ($OD_{600}$) was assessed immediately after inoculation and again after 18 hours using Biotek Synergy II microplate reader. The MIC was defined as the lowest concentration that inhibited growth to a level greater than or equal to 90% (for $MIC_{90}$) or greater than or equal to 50% (for $MIC_{50}$) by comparison to untreated cultures.

FIG. 11A-F illustrates biofilm formation by various strains of *Staphylococcus* in the absence or presence of various concentration of caffeic acid, ellagic acid, ferulic acid, gallic acid, kaempferol, oleanolic acid, quercetin dihydrate, and ursolic acid. The results for all 10 compounds are presented in Table 4. The only compound exhibiting meaningful anti-biofilm activity at doses well below any growth inhibitory effects was ellagic acid (EA) (Table 4). This finding supports the hypothesis that EA and EADs present in 220D-F2 are responsible for the anti-biofilm properties of the extract.

TABLE 4

Inhibitory Effects of Individual Phytochemicals.

| | Biofilm Formation | | Growth | |
| --- | --- | --- | --- | --- |
| Compound | $MBIC_{50}$ (μM) | $MBIC_{90}$ (μM) | $MBIC_{50}$ (μM) | $MBIC_{90}$ (μM) |
| Caffeic Acid | >2000 | >2000 | >2000 | >2000 |
| Ellagic Acid | 38 ± 13 | 763 ± 32 | >2000 | >2000 |
| Ferulic Acid | >2000 | >2000 | >2000 | >2000 |
| Gallic Acid | 713 ± 32 | 2010 ± 10 | >2000 | >2000 |

TABLE 4-continued

Inhibitory Effects of Individual Phytochemicals.

| Compound | Biofilm Formation | | Growth | |
|---|---|---|---|---|
| | $MBIC_{50}$ (μM) | $MBIC_{90}$ (μM) | $MBIC_{50}$ (μM) | $MBIC_{90}$ (μM) |
| Kaempferol | 560 ± 53 | 773 ± 6 | 1640 ± 10 | 1787 ± 42 |
| Oleanolic Acid | 190 ± 26 | 940 ± 35 | 1077 ± 15 | 1613 ± 31 |
| Quercetin Dihydrate | 543 ± 21 | 1987 ± 21 | 1720 ± 20 | 1903 ± 29 |
| Ursolic Acid | 207 ± 32 | 397 ± 6 | 640 ± 46 | 763 ± 32 |

TABLE 4-continued

Inhibitory Effects of Individual Phytochemicals.

| Compound | Biofilm Formation | | Growth | |
| --- | --- | --- | --- | --- |
| | $MBIC_{50}$ (µM) | $MBIC_{90}$ (µM) | $MBIC_{50}$ (µM) | $MBIC_{90}$ (µM) |
| Quercetin-3-O-glucuronide | >2000 | >2000 | >2000 | >2000 |

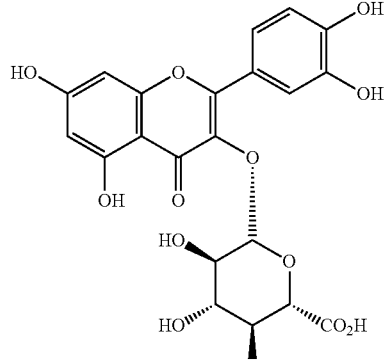

| | | | | |
| --- | --- | --- | --- | --- |
| Tiliroside | >2000 | >2000 | >2000 | >2000 |

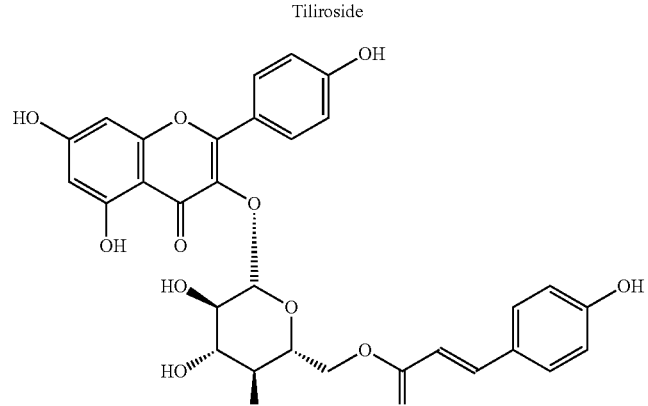

Example 8

Biofilm Inhibition in the Presence and Absence of Human Plasma Proteins

Previous studies have indicated that ellagic acid is not an effective biofilm inhibitor for *S. aureus* (See Durig et al., Applied Microbiology and Biotechnology 87: 309-317, 2010). The methicillin-sensitive strain UAMS-1 (USA200) and the methicillin-resistant strain UAMS-1782 (USA300) were used to assess the efficacy of 220D-F2 and ellagic acid in experiments that included or omitted the use of plasma coating for the test wells. Treatment with 220D-F2 elicited a dose-dependent response in limiting biofilm formation under both growth conditions (data not shown). This suggests that the anti-biofilm activity of 200D-F2 is not due to EA alone, but rather other constituent(s) present in the extract must also play a role that may involve other mechanisms, which have not yet been elucidated.

Example 9

Cytotoxicity of 220D-F2 on Normal Mammalian Cells

To examine the cytotoxic effects of 220D-F2 on normal mammalian liver and kidney cells, a lactate dehydrogenase (LDH) assay was employed. LDH is a stable cytosolic enzyme that is released upon membrane damage in necrotic cells. LDH activity can serve as a useful measure for determining drug toxicity to cell lines.

LDH was measured using a commercial cytotoxicity assay kit (Promega CytoTox 96® Non-Radioactive Cytotoxicity Assay, WI, USA), in which LDH released in culture supernatants is measured with a coupled enzymatic assay, resulting in conversion of a tetrazolium salt into a red formazan product. The cells were treated with concentrations of extract 220D-F2 ranging from 0.1-7,000 µg/mL and incubated in humidified air with 5% $CO_2$ at 37° C. for 24 hours. Controls for the extract excipient (20% DMSO in phosphate buffered saline, PBS), positive LDH control, and positive LDH control with media and extract were also included. The sample solution (supernatant) was removed, and the LDH released from the cells into culture medium treated according to kit instructions, then measured at an OD490 nm. The maximal release was obtained after treating cells with a lysis solution for 45 minutes, then treating the supernatant according to kit instructions. All tests were performed in quadruplicate. The necrotic percentage (% cytotoxicity) was expressed using the formula: (sample value/maximal release)×100%.

Normal human kidney proximal tubular (HK-2) cells, normal rat kidney (NRK-52E) cells, normal mouse hepatocytes (AML12), and normal mouse kidney proximal tubular cells (TKPTS) were cultured with different media: keratinocyte serum free media (K-SFM) supplemented with bovine pituitary extract (BPE) and human recombinant epidermal growth factor (EGF) for HK-2 cells; Dubelcco's Modified Eagle's Medium (DMEM) for NRK-52E cells; and ATCC complete growth medium (1:1 mix of DMEM and Ham's F12 medium supplemented with insulin, transferring, dexamethasone, and fetal bovine serum) for AML2 and TKPTS cells. Cells were maintained in humidified air with 5% $CO_2$ at 37° C. Cells were transferred to 96-well cell culture plates (10,000 cells seeded per well) and incubated for 24 hours prior to aspirating the media, adding extract 220D-F2 in serum-free media and undertaking cytotoxicity tests.

Figure 12:
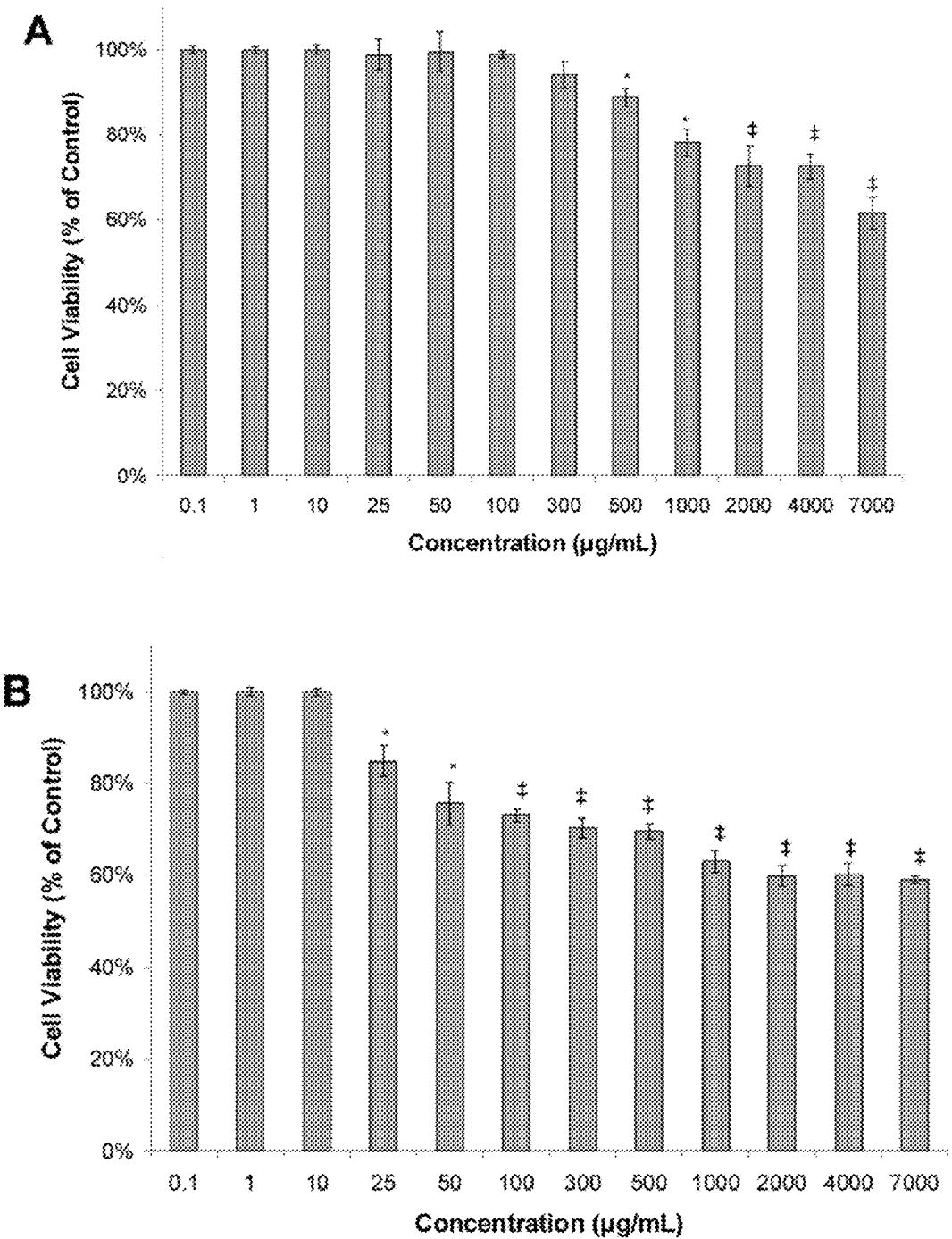
FIG. 12 shows the results of cytotoxicity testing using a lactate dehydrogenase (LDH) test following 24 hours of exposure to fraction 220D-F2. Results are reported as the percent of cell viability after exposure to the indicated dosage of 220D-F2 in the culture growth medium. Statistical significance (*, $P<0.05$; ‡, $P<0.001$) refers to differences observed in comparison to the untreated (excipient) control. (A) shows results against normal human kidney proximal tubular (HK-2) cells. (B) shows results against normal mouse kidney proximal tubular (TKPTS) cells. (C) shows results against normal rat kidney (NRK-52E) cells. (D) shows results against normal mouse hepatocytes (AML12).
Figure 12:
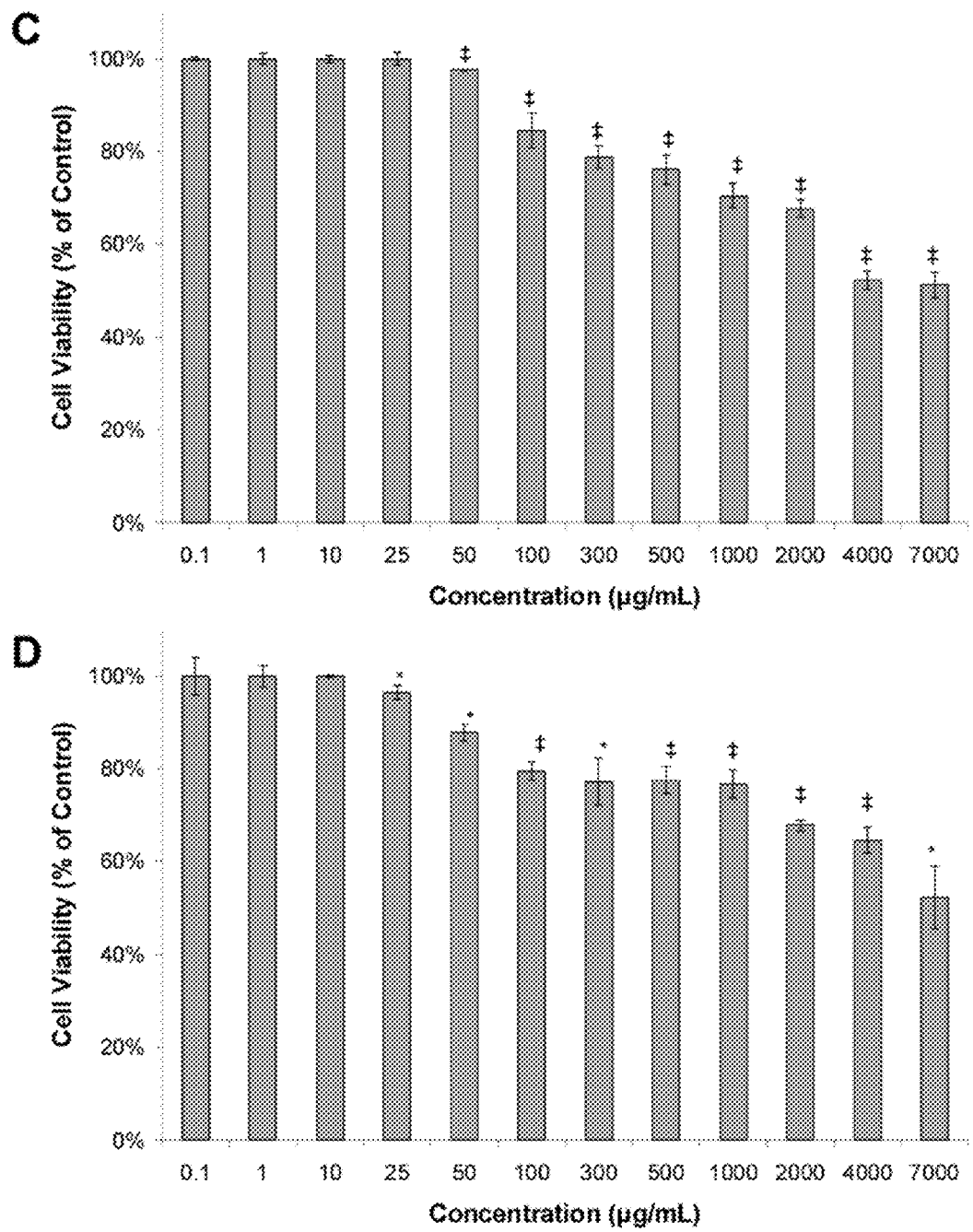

Results are reported as the percent of cell viability after exposure to the indicated dosage of 220D-F2 in the culture growth medium (FIG. 12). Normal human (HK-2) and mouse (TKPTS) proximal tubular kidney cells demonstrated very good tolerance for the extract, and no $IC_{50}$ could be identified even at extremely high doses of 7,000 µg/mL. Rat kidney (NRK-52E) cells and mouse hepatocytes (AML-12) were slightly more sensitive and had $IC_{50s}$ of 4,000 and 7,000 µg/mL, respectively. Human kidney cells were the least impacted and a significant effect in decreasing cell viability was notable only at concentrations ≥500 µg/mL. These results are relevant as the active doses for biofilm inhibition range from 50-200 µg/mL (depending on the *S. aureus* strain) and no or very limited impact (<20%) on cell viability was notable at these concentrations in the cell lines examined.

What is claimed is:

1. A medical device having a coating comprising a polyphenolic composition comprising at least one glycosylated derivative of ellagic acid chosen from ellagic acid xylofuranoside, ellagic acid mannopyranoside, ellagic acid rhamnoside, or combination thereof.

2. The medical device of claim 1, wherein the polyphenolic composition further comprises ellagic acid.

3. The medical device of claim 2, wherein the polyphenolic composition further comprises at least one sapogenin.

4. The medical device of claim 1, wherein the medical device is an implantable medical device.

5. The medical device of claim 4, wherein the implantable medical device is chosen from a catheter, a cardiac device, an orthopedic device, a breathing tube, or a feeding tube.

6. The medical device of claim 1, wherein the coating further comprises an antimicrobial agent chosen from an antibiotic, an antifungal agent, or an antiseptic.

7. The medical device of claim 6, wherein the antimicrobial agent is an antibiotic chosen from amphotericin B, clindamycin, daptomycin, dicloxicillin, minocycline, nafcillin, oxacillin, ramoplanin, rifampin, triclosan, or vancomycin.

8. The medical device of claim 1, wherein the coating comprises a hydrogel.

* * * * *